United States Patent
Heyn et al.

(10) Patent No.: US 7,094,373 B2
(45) Date of Patent: Aug. 22, 2006

(54) PROCESS AND APPARATUS FOR AIR FORMING AN ARTICLE HAVING A PLURALITY OF REINFORCED SUPERIMPOSED FIBROUS LAYERS

(75) Inventors: David W. Heyn, Neenah, WI (US); Susan J. Daniels, Neenah, WI (US); Derek Paul Murphy, Menasha, WI (US); Michael Barth Venturino, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 405 days.

(21) Appl. No.: 10/305,755

(22) Filed: Nov. 27, 2002

(65) Prior Publication Data

US 2004/0061264 A1 Apr. 1, 2004

Related U.S. Application Data

(63) Continuation-in-part of application No. 10/255,660, filed on Sep. 26, 2002.

(51) Int. Cl.
*B29C 59/00* (2006.01)
*B29C 59/02* (2006.01)
*B29C 69/00* (2006.01)

(52) U.S. Cl. .............. 264/101; 264/113; 264/172.9; 264/263; 264/271.1; 425/81.1; 425/83.1; 425/405.1

(58) Field of Classification Search ............... 264/101, 264/113, 172.9, 263, 271.1; 425/81.1, 83.1, 425/40.511
See application file for complete search history.

(56) References Cited

U.S. PATENT DOCUMENTS

| 2,161,539 | A | 6/1939 | Swartz |
| 2,964,039 | A | 12/1960 | Johnson, Jr. et al. |
| 3,085,309 | A | 4/1963 | Olson |
| 3,156,751 | A | 11/1964 | Valdes et al. |
| 3,587,579 | A | 6/1971 | Sabee |
| 3,629,047 | A | 12/1971 | Davison |

(Continued)

FOREIGN PATENT DOCUMENTS

| AU | 458424 | 2/1975 |
| DE | 198 23 954 A1 | 12/1999 |

(Continued)

OTHER PUBLICATIONS

International Search Report, dated Jul. 29, 2003 in PCT/US 03/00294, 3 pages.
International Search Report for PCT/US 03/00293 dated Jul. 29, 2003.

(Continued)

*Primary Examiner*—Stephen J. Lechert, Jr.
(74) *Attorney, Agent, or Firm*—Senniger Powers

(57) ABSTRACT

A process and apparatus for air forming an article having a plurality of superimposed reinforced fibrous layers. The layers are formed in substantially discrete forming chambers by depositing fibrous materials on a forming surface which moves along a forming path through the chambers. A first layer is air-formed on the forming surface as the surface moves through the first forming chamber and a second layer is air-formed over the first layer as the surface moves through the second forming chamber. A reinforcing web is embedded in the article during the air-forming process.

22 Claims, 17 Drawing Sheets

U.S. PATENT DOCUMENTS

| | | | |
|---|---|---|---|
| 3,683,921 A | 8/1972 | Brooks et al. | |
| 3,768,479 A | 10/1973 | Widlund | |
| 3,816,231 A | 6/1974 | Marshall | |
| 3,856,012 A | 12/1974 | MacDonald et al. | |
| 3,862,877 A | 1/1975 | Camden | |
| 3,867,935 A | 2/1975 | Eisdorfer et al. | |
| 3,888,248 A | 6/1975 | Moore et al. | |
| 3,935,979 A | 2/1976 | Hickey | |
| 4,001,472 A | 1/1977 | Thomas et al. | |
| 4,028,455 A | 6/1977 | Ueda et al. | |
| 4,141,772 A | 2/1979 | Buell | |
| 4,217,078 A | 8/1980 | Buell | |
| 4,235,237 A | 11/1980 | Mesek et al. | |
| 4,300,562 A | 11/1981 | Pieniak | |
| 4,303,189 A | 12/1981 | Wiley et al. | |
| 4,392,862 A | 7/1983 | Marsan et al. | |
| 4,425,127 A | 1/1984 | Suzuki et al. | |
| 4,606,964 A | 8/1986 | Wideman | |
| 4,666,647 A | 5/1987 | Enloe et al. | |
| 4,674,966 A | 6/1987 | Johnson et al. | |
| 4,704,112 A | 11/1987 | Suzuki et al. | |
| 4,710,185 A | 12/1987 | Sneyd, Jr. et al. | |
| 4,761,258 A | 8/1988 | Enloe | |
| 4,764,325 A | 8/1988 | Angstadt | |
| 4,765,780 A | 8/1988 | Angstadt | |
| 4,773,903 A | 9/1988 | Weisman et al. | |
| 4,775,579 A | 10/1988 | Hagy et al. | |
| 4,810,568 A | 3/1989 | Buyofsky et al. | |
| 4,837,715 A | 6/1989 | Ungpiyakul et al. | |
| 4,904,440 A | 2/1990 | Angstadt | |
| 4,908,175 A | 3/1990 | Angstadt | |
| 4,915,897 A | 4/1990 | Farrington et al. | |
| 4,915,993 A | 4/1990 | Ten Wolde | |
| 4,927,346 A * | 5/1990 | Kaiser et al. | 425/81.1 |
| 4,927,582 A | 5/1990 | Bryson | |
| 5,004,579 A | 4/1991 | Wislinski et al. | |
| 5,017,324 A * | 5/1991 | Kaiser et al. | 264/510 |
| 5,124,188 A | 6/1992 | Roe et al. | |
| 5,128,082 A | 7/1992 | Makoui | |
| 5,139,841 A | 8/1992 | Makoui et al. | |
| 5,144,729 A | 9/1992 | Austin et al. | |
| 5,161,283 A | 11/1992 | Hansen | |
| 5,219,633 A | 6/1993 | Sabee | |
| 5,281,208 A | 1/1994 | Thompson et al. | |
| 5,302,445 A | 4/1994 | DePetris et al. | |
| 5,328,072 A | 7/1994 | Ruessmann et al. | |
| 5,334,446 A | 8/1994 | Quantrille et al. | |
| 5,389,095 A | 2/1995 | Suzuki et al. | |
| 5,389,202 A * | 2/1995 | Everhart et al. | 162/103 |
| 5,429,788 A * | 7/1995 | Ribble et al. | 264/510 |
| 5,447,677 A | 9/1995 | Griffoul et al. | |
| 5,466,409 A | 11/1995 | Partridge et al. | |
| 5,486,167 A | 1/1996 | Dragoo et al. | |
| 5,505,720 A | 4/1996 | Walters et al. | |
| 5,527,300 A | 6/1996 | Sauer | |
| 5,531,729 A | 7/1996 | Coles et al. | |
| 5,591,148 A | 1/1997 | McFall et al. | |
| 5,607,415 A | 3/1997 | Datta et al. | |
| 5,614,283 A | 3/1997 | Potnis et al. | |
| 5,622,581 A | 4/1997 | Ducker et al. | |
| 5,672,306 A * | 9/1997 | Sprang et al. | 264/136 |
| 5,704,931 A | 1/1998 | Holtman et al. | |
| 5,756,039 A | 5/1998 | McFall et al. | |
| 5,762,844 A | 6/1998 | Van Himbergen et al. | |
| 5,772,813 A | 6/1998 | Bitowft et al. | |
| 5,803,334 A | 9/1998 | Patel et al. | |
| 5,818,719 A | 10/1998 | Brandon et al. | |
| 5,866,173 A | 2/1999 | Reiter et al. | |
| 5,871,613 A | 2/1999 | Bost et al. | |
| 5,873,963 A | 2/1999 | Trombetta et al. | |
| 5,902,757 A | 5/1999 | Stern et al. | |
| 5,916,661 A | 6/1999 | Benson et al. | |
| 5,925,439 A | 7/1999 | Haubach | |
| 5,938,648 A | 8/1999 | LaVon et al. | |
| 5,944,706 A | 8/1999 | Palumbo et al. | |
| 5,947,945 A | 9/1999 | Cree et al. | |
| 5,961,509 A | 10/1999 | Kling | |
| 5,997,520 A | 12/1999 | Ahr et al. | |
| 6,048,489 A | 4/2000 | Reiter et al. | |
| 6,060,637 A | 5/2000 | Bitowft et al. | |
| 6,107,538 A | 8/2000 | Young et al. | |
| 6,203,654 B1 | 3/2001 | McFall et al. | |
| 6,204,207 B1 | 3/2001 | Cederblad et al. | |
| 6,220,999 B1 | 4/2001 | Kugler et al. | |
| 6,258,996 B1 | 7/2001 | Goldman | |
| 6,262,331 B1 | 7/2001 | Nakahata et al. | |
| 6,284,943 B1 | 9/2001 | Osborn, III et al. | |
| 6,296,862 B1 | 10/2001 | Paul et al. | |
| 6,330,735 B1 | 12/2001 | Hahn et al. | |
| 6,375,644 B1 | 4/2002 | Mizutani | |
| 6,416,697 B1 | 7/2002 | Venturino et al. | |
| 6,492,574 B1 | 12/2002 | Chen et al. | |
| 6,533,978 B1 | 3/2003 | Wisneski et al. | |
| 6,533,989 B1 | 3/2003 | Wisneski et al. | |
| 6,630,096 B1 | 10/2003 | Venturino et al. | |
| 2001/0039405 A1 | 11/2001 | Keuhn, Jr. et al. | |
| 2003/0116888 A1 | 6/2003 | Rymer et al. | |
| 2003/0119401 A1 | 6/2003 | Chakravarty et al. | |
| 2003/0132556 A1 | 7/2003 | Venturino et al. | |
| 2003/0139721 A1 | 7/2003 | Melius et al. | |
| 2004/0102752 A1 | 5/2004 | Chen et al. | |

FOREIGN PATENT DOCUMENTS

| | | |
|---|---|---|
| EP | 0 151 018 A2 | 8/1985 |
| EP | 0 226 939 A2 | 12/1986 |
| EP | 0 297 180 B1 | 1/1989 |
| EP | 0 298 348 A1 | 11/1989 |
| EP | 0 399 511 A2 | 11/1990 |
| EP | 0 467 409 A1 | 1/1992 |
| GB | 2168612 A | 6/1986 |
| JP | 09122172 | 5/1997 |
| JP | 10211236 | 8/1998 |
| WO | WO 93/18729 A1 | 9/1993 |
| WO | WO 96/00550 A1 | 1/1996 |
| WO | WO 99/22685 A1 | 5/1999 |
| WO | WO 99/25281 A1 | 5/1999 |
| WO | WO 00/10498 A1 | 3/2000 |
| WO | WO 00/37000 A1 | 6/2000 |
| WO | WO 00/37725 A1 | 6/2000 |
| WO | WO 00/63479 A1 | 10/2000 |
| WO | WO 01/92003 A1 | 12/2001 |
| WO | WO 03/059232 A2 | 7/2003 |

OTHER PUBLICATIONS

International Search Report for PCT/US 03/01337 dated Jul. 21, 2003.
International Search Report for PCT/US 03/16480 dated Oct. 2, 2003.
Partial International Search Report for PCT/US 03/15959, dated Oct. 16, 2003.
International Search Report, dated May 28, 2003 in PCT/US 03/00881, 8 pages.
International Search Report for PCT/US 03/16480 dated Oct. 2, 2003.
International Search Report for PCT/US2004/008428 dated Aug. 23, 2004, 4 pages.
International Search Report for PCT/US2004/006915 dated Nov. 5, 2004, 7 pages.

* cited by examiner

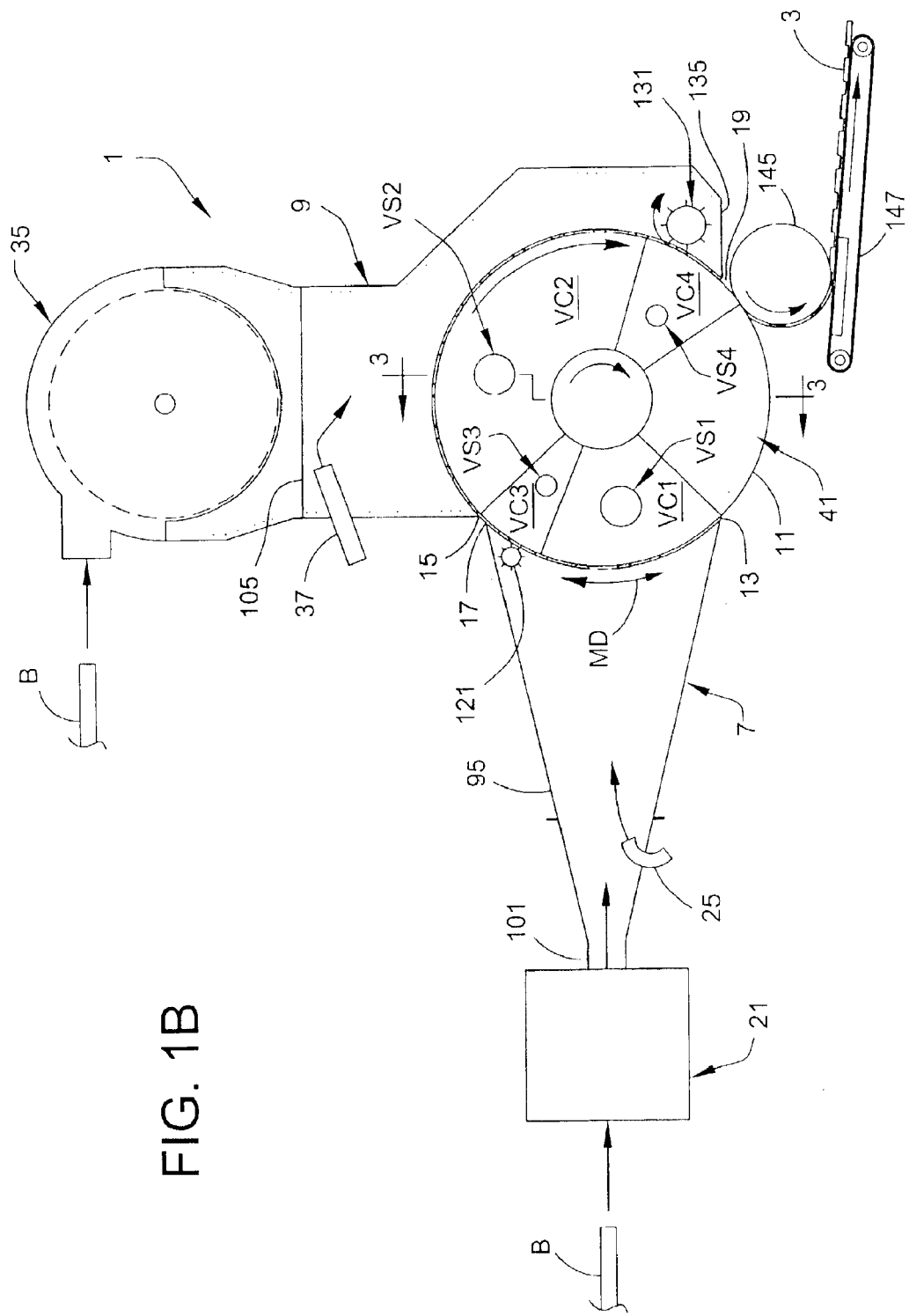

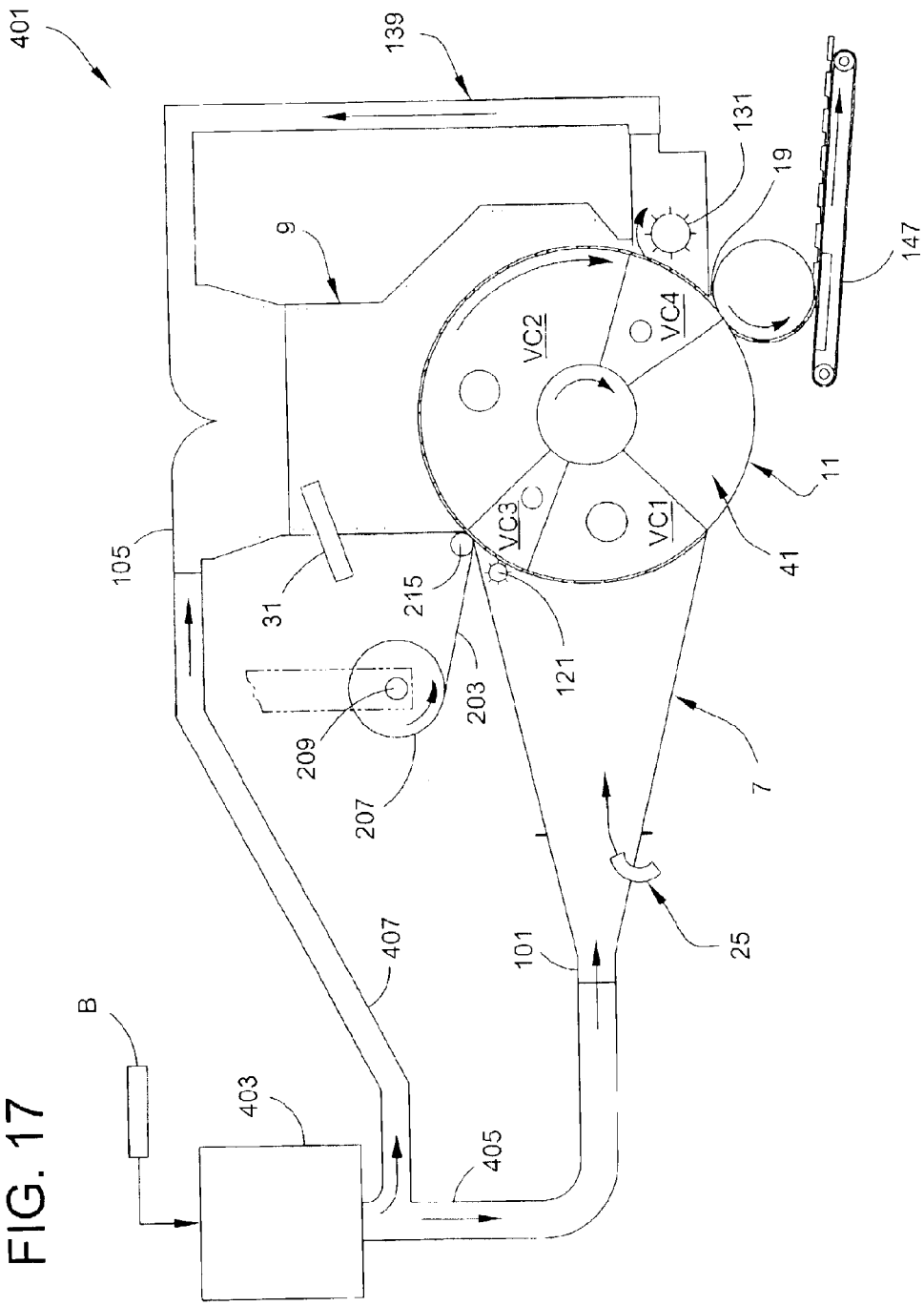

PROCESS AND APPARATUS FOR AIR FORMING AN ARTICLE HAVING A PLURALITY OF REINFORCED SUPERIMPOSED FIBROUS LAYERS

REFERENCE TO RELATED APPLICATIONS

This application is a continuation-in-part of pending co-assigned application Ser. No. 10/255,660, filed Sep. 26, 2002, entitled "Process and Apparatus for Air Forming an Article Having a Plurality of Superposed Fibrous Layers", by Daniels et al.

BACKGROUND OF THE INVENTION

This invention relates generally to a process and apparatus for making an air formed article having more than one layer, and more particularly to such an article which is constructed of fibrous material having a reinforcing web incorporated therein for use as an absorbent core for applications such as disposable diapers, child's training pants, feminine care articles, incontinence articles, and the like.

In the general practice of forming fibrous articles, it has been common to use a fibrous sheet of cellulosic or other suitable absorbent material which has been fiberized in a conventional fiberizer, or other shredding or comminuting device, to form discrete fibers. In addition, particles of superabsorbent material have been mixed with the fibers. The fibers and superabsorbent particles have then been entrained in an air stream and directed to a foraminous forming surface upon which the fibers and superabsorbent particles have been deposited to form an absorbent fibrous member, such as an absorbent core to be used as part of one of the aforementioned articles. An absorbent core formed in this fashion has a liquid holding formation which is intended to be the primary repository for liquid to be held by the absorbent core. Thus, the liquid holding formation has conventionally been formed to have a greater amount of fibrous and superabsorbent material (SAM) than surrounding regions and is generally thicker than the surrounding regions of fibrous material. In addition, bonding agents or other strengthening components may be incorporated to provide a stabilized absorbent member. The absorbent member may then be stored or immediately directed for further processing and assembly with other components to produce an absorbent article. Other conventional techniques, such as dry-forming techniques, wet-laying techniques, foam-forming techniques, and various wet-forming techniques, have also been employed to form stabilized absorbent members. The resulting absorbent members have included absorbent fibers, natural fibers, synthetic fibers, superabsorbent materials, binders, and strengthening components in desired combinations.

Absorbent members may also be strengthened by adding reinforcing materials, such as reinforcement filaments, tissue layers, fabric layers and netting materials to the fibrous material. For example, co-assigned U.S. patent application Ser. No. 10/306,086 entitled "Absorbent Article with Reinforced Absorbent Structure" by David W. Heyn et al., discloses a reinforced fibrous absorbent member comprised of a fibrous material and a scrim (e.g., netting or mesh material) incorporated within the fibrous material to strengthen the absorbent member and reduce the risk of cracking thereof during use. The entire disclosure of the aforementioned application is incorporated herein by reference in a manner consistent herewith.

Some absorbent members are formed as a laminate, i.e., a structure having two or more layers. Conventional systems capable of making such articles typically comprise two or more complete independent forming systems, one system for forming each layer after which the layers are combined to make the article. Because the fibers are not substantially commingled at the interface between adjacent layers, the flow of liquid across the interface is inhibited, which is undesirable. The use of such systems also typically requires a large capital expenditure, and space requirements make such systems costly and often undesireable. Further, the implementation of two forming systems requires phase adjustments between the two systems to ensure that the product components by the systems are in proper registration with respect to one another in the final product. If the systems are out of phase, defective products are manufactured and waste is induced, further increasing manufacturing costs.

There is a need, therefore, for a process and apparatus which overcomes the problems associated with the prior art systems mentioned above, and which provides for the economical manufacture of articles such as fibrous absorbent members having multiple layers reinforced by a web embedded in the layers.

SUMMARY OF THE INVENTION

Apparatus of this invention is used for air forming a reinforced fibrous article having a plurality of layers. The apparatus comprises first and second substantially discrete forming chambers, each forming chamber having an entrance and exit. A foraminous forming surface is movable through the first and second forming chambers along a forming path length. A first fiber inlet is provided for introducing a fibrous material into the first forming chamber, and a second fiber inlet is provided for introducing a fibrous material into the second forming chamber. One or more vacuum sources are in communication with the first and second forming chambers for drawing fibrous material in the first forming chamber onto the forming surface to form a first layer on the forming surface and for drawing fibrous material in the second forming chamber onto the forming surface to form a second layer on the forming surface over the first layer. A source of reinforcing web is located generally exterior to the first and second forming chambers. A delivery mechanism operates to deliver reinforcing web from the source for application of the web to the forming surface at a location along the forming path length.

A process of this invention comprises moving a foraminous forming surface through first and second substantially discrete forming chambers along a forming path length, each forming chamber having an entrance and exit. Fibrous material introduced into the first forming chamber is vacuum drawn onto the forming surface to form a first layer on the forming surface. Fibrous material introduced into the second forming chamber is vacuum drawn onto the forming surface to form a second layer superimposed on the first layer. Reinforcing web is overlaid on fibers collected on the forming surface at a location along the forming path.

Other objects and features will be in part apparent and in part pointed out hereinafter.

BRIEF DESCRIPTION OF THE DRAWINGS

FIG. 1B is a view similar to FIG. 1 but showing a third embodiment of the apparatus;

FIG. 17 is a view similar to FIG. 10 but showing apparatus having a different fiber feed configuration.

Corresponding reference characters indicated corresponding parts throughout the several views of the drawings.

DETAILED DESCRIPTION OF THE DRAWINGS

Figure 1:
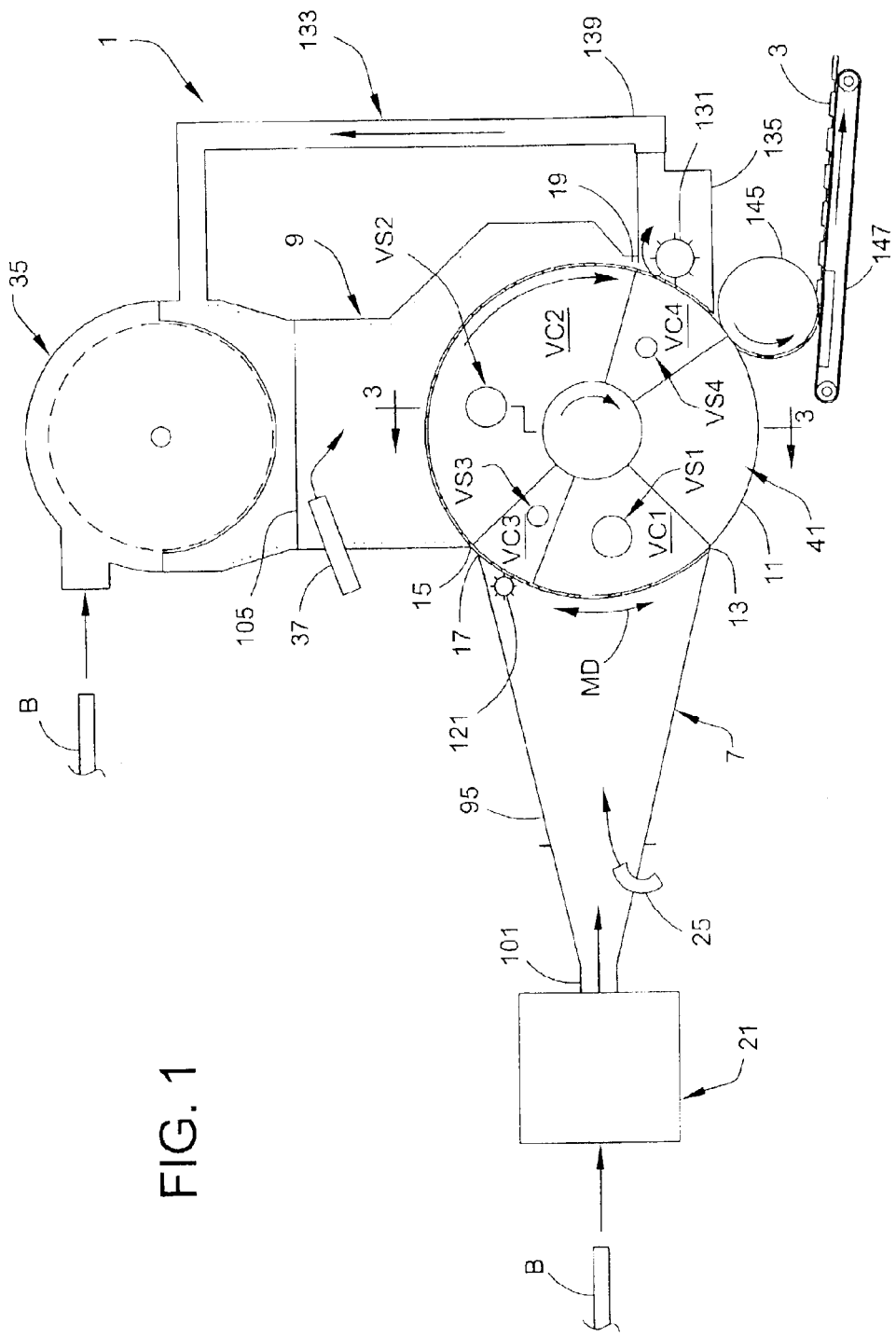
FIG. 1 is a schematic, side elevation of a dual-chamber air forming apparatus for forming fibrous articles having first and second layers.

The present invention is generally directed to a process and apparatus, indicated generally as 1 in FIG. 1, for making a fibrous article 3, comprising multiple layers of fibrous material and/or other particulate material. In particular aspects, the article 3 can be an absorbent member used as an absorbent core within disposable personal care products such as diapers, children's training pants, adult incontinence products, feminine care products, medical garments, bandages and the like. As described herein, the article 3 has two layers, designated L1 and L2, but it will be understood that the present invention can be employed to form a member with more than two layers.

For the purpose of describing the present invention, the apparatus 1 has an appointed machine-direction MD (FIG. 1) extending generally in a direction that the absorbent member, or a particular component or material thereof, is transported lengthwise along and through a particular, local position of the apparatus. A cross-machine direction CD (FIG. 3) of the apparatus 1 lies generally within the plane of the article 3, or particular component or material thereof, and is transverse to the machine-direction MD. A Z-direction ZD of the apparatus 1 is substantially perpendicular to both the machine-direction MD and the cross-machine direction CD, and extends generally along a depthwise, thickness dimension of the article 3 formed by the apparatus.

In general, apparatus 1 comprises first and second substantially discrete forming chambers, designated 7 and 9, respectively, and a foraminous forming surface 11 movable through the two chambers along a forming path P. The first and second chambers have entrances designated 13 and 15, respectively, where the forming surface 11 enters the chambers, and exits designated 17 and 19, respectively, where the forming surface exits the chambers. As used herein, the "forming path length" means the length of the path P from the entrance 13 of the first forming chamber 7 to the exit 19 of the second forming chamber 9. (If more than two forming chambers are used, the forming path length is the length of the forming path P from the entrance 13 of the first forming chamber 7 to the exit of the last forming chamber along the path.) The apparatus 1 also includes a first fiber feed mechanism 21 for introducing a fibrous material into the first forming chamber 7, and a first superabsorbent feed mechanism 25 for introducing a superabsorbent material into the first forming chamber. A first vacuum source, generally indicated at VS1, communicates with the first forming chamber 7 for drawing fibrous material and superabsorbent material in the first forming chamber onto the forming surface 11 to form a first layer L1 on the forming surface. In accordance with one aspect of the present invention, the apparatus 1 further comprises a second fiber feed mechanism 35 for introducing a fibrous material into the second forming chamber 9, and a second superabsorbent feed mechanism 37 for introducing a superabsorbent material into the second forming chamber 9. A second vacuum source, generally designated VS2, communicates with the second forming chamber 9 for drawing fibrous material and superabsorbent material in the second forming chamber onto the forming surface 11 to form a second layer L2 on the forming surface superimposed on the first layer. Third and fourth vacuum sources VS3, VS4 are also provided for holding one or both layers L1, L2 on the forming surface 11 as it moves, as will be described in more detail hereinafter.

Figure 3:
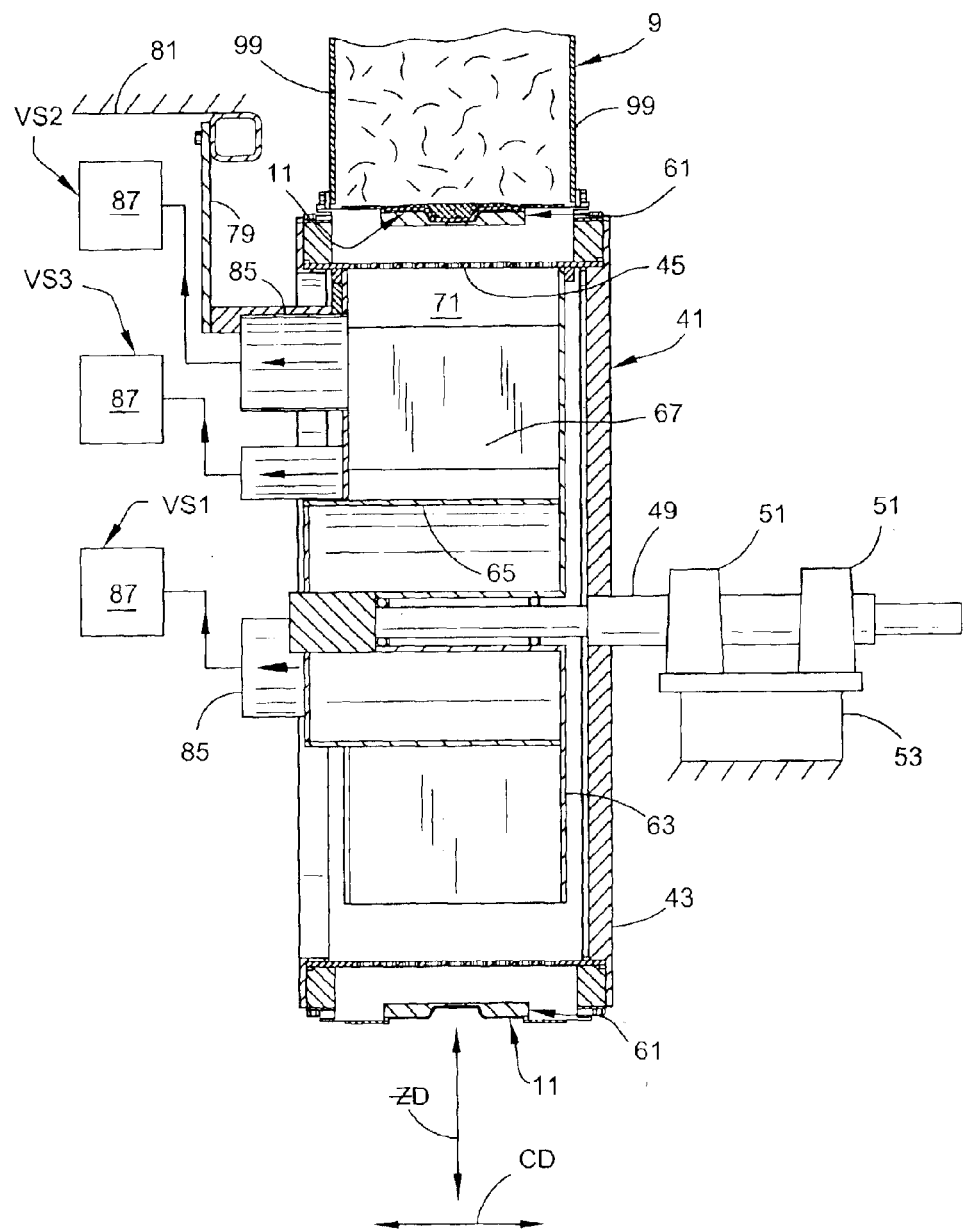
FIG. 3 is an enlarged sectional view taken in the plane of 3—3 of FIG. 1.
Figure 4:
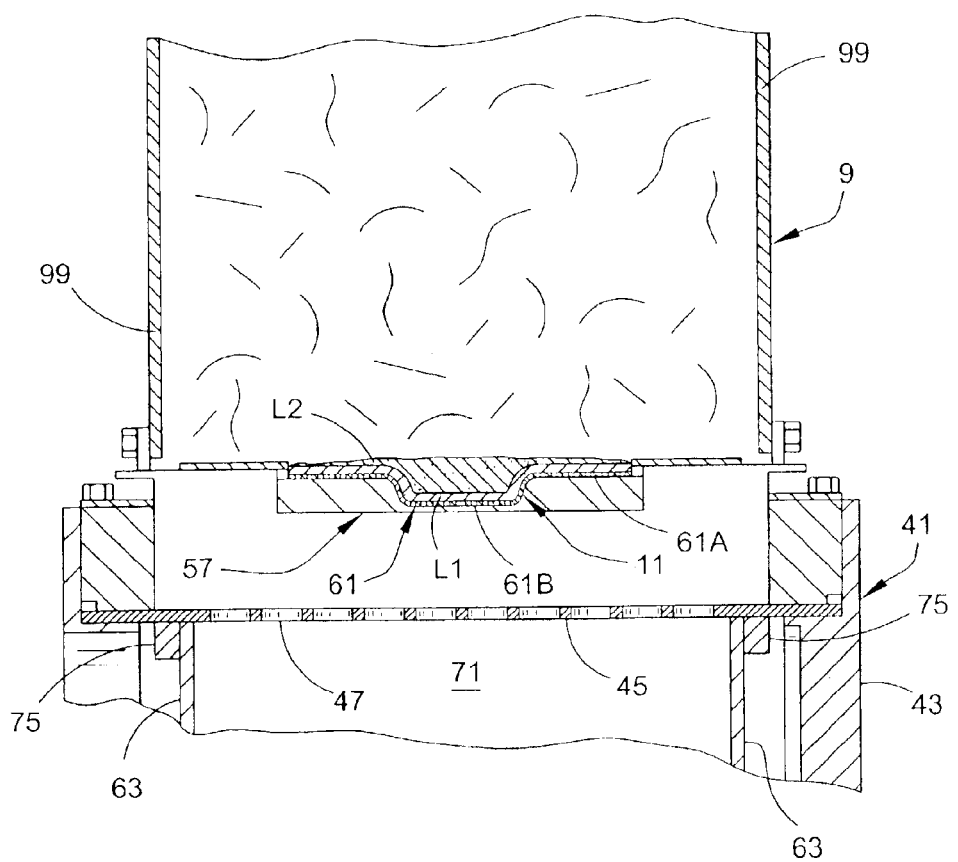
FIG. 4 is an enlarged sectional view taken in the plane of 4—4 of FIG. 2.

In the preferred embodiment, the foraminous forming surface 11 extends around the circular circumference of a drum 41. As illustrated in FIGS. 3 and 4, the drum 41 includes a circular wall 43 and an outer annular rim 45 extending as a cantilever from the wall for supporting the forming surface 11. The drum rim has a multiplicity of holes 47 over its surface area to provide a substantially free movement of fluid, such as air, through the thickness of the rim. The drum is rotatably mounted on a shaft 49 connected by bearings 51 to a support 53. The shaft 49 is rotatably driven by a suitable motor or line shaft (not shown) in a clockwise direction in the illustrated embodiment of FIG. 1.

Figure 5:
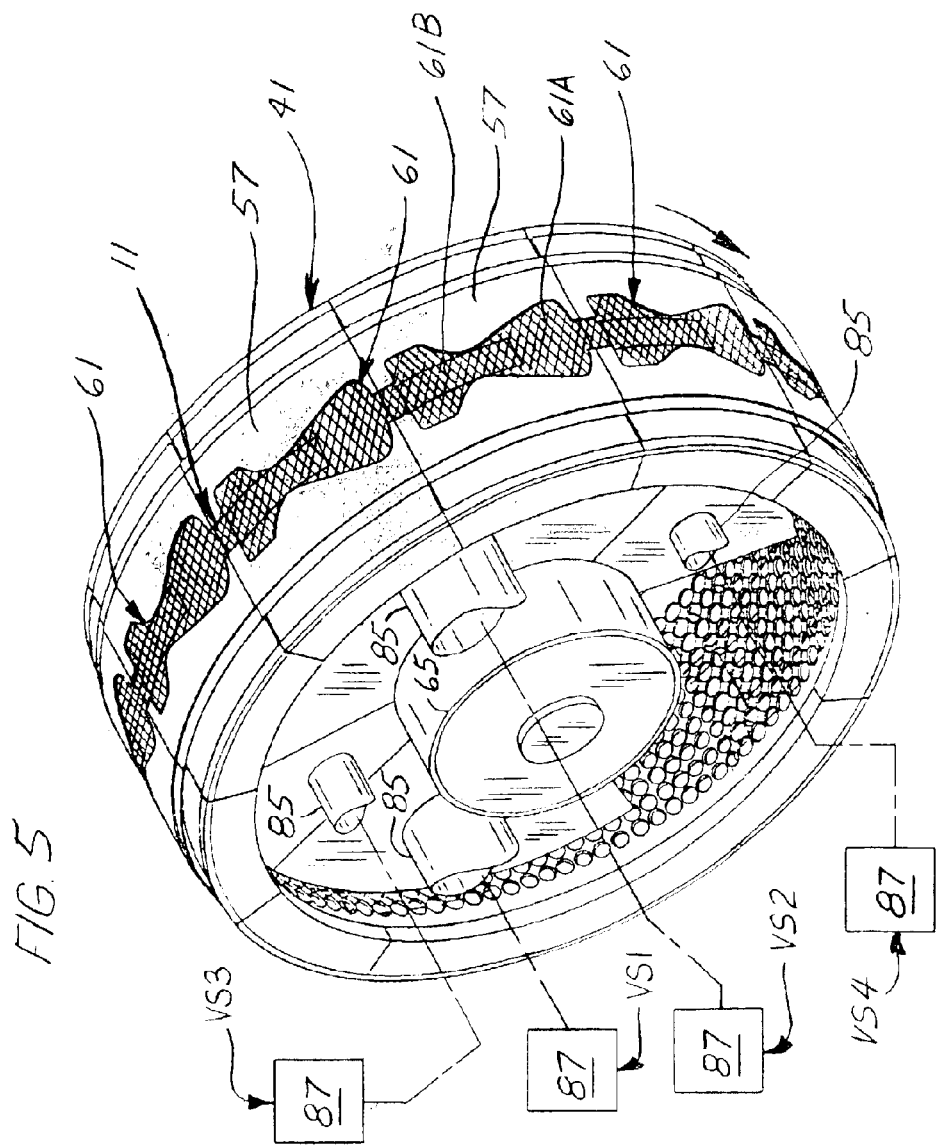
FIG. 5 is a schematic perspective of a forming drum of the apparatus of FIG. 1.

The foraminous forming surface 11 is defined in the illustrated embodiment (FIG. 5) by a series of form members 57 which are arranged end-to-end around the periphery of the forming drum 41 and independently attached to the drum. As may be seen in FIG. 5, each form member 57 has a formaminous area 61 fabricated from wire mesh or the like defining a pattern in which fibrous material is collected. The patterns on the form members are preferably substantially identical and correspond to a desired shape of individual articles 3 which repeats over the circumference of the drum 41. However, partially repeating or non-repeating pattern shapes may be used with the present invention. It is also understood that a continuous, un-patterned article may be formed on the forming surface, such as where the forming surface is flat or where the formed article is generally rectangular, and is subsequently processed (e.g., cut or otherwise formed) to a desired shape. In the embodiment shown in FIGS. 4 and 5, each foraminous area 61 has a first section 61A for collecting fibrous material to a first depth and second section or pocket 61B for collecting fibrous material to a second depth greater than the stated first depth. The material collected in the pocket section 61B typically constitutes a liquid holding formation intended to be the primary repository for liquid to be held by the article.

For additional detail regarding the construction of an exemplary forming surface, reference may be made to pending U.S. patent application Ser. No. 10/207,929, entitled APPARATUS AND FORM FOR MAKING AN AIR FORMED FIBROUS WEB by Venturino et al., filed Jul. 30, 2002, U.S. patent application Ser. No. 09/694,374, entitled FORMING MEDIA WITH ENHANCED AIR FLOW PROPERTIES by Michael B. Venturino et al., filed Oct. 23, 2000, and to U.S. Pat. No. 6,330,735, entitled APPARATUS AND PROCESS FOR FORMING A LAID FIBROUS WEB WITH ENHANCED BASIS WEIGHT CAPABILITY, by John Timothy Hahn et al., assigned to Kimberly-Clark Worldwide, Inc., the entire disclosures of which are incorporated by reference in a manner consistent herewith. It will be understood, however, that the principles of the present invention can be practiced with different foraminous forming surfaces.

The forming surface 11 is illustrated herein as being part of the forming drum 41, but it is to be understood that other techniques for providing the foraminous forming surface 11 may also be employed without departing from the scope of the present invention. For example, the forming surface may be provided by an endless forming belt (not shown). A forming belt of this type is shown in U.S. Pat. No. 5,466,409, entitled FORMING BELT FOR THREE-DIMENSIONAL FORMING APPLICATIONS by M. Partridge et al. which issued on Nov. 14, 1995.

Figure 6:
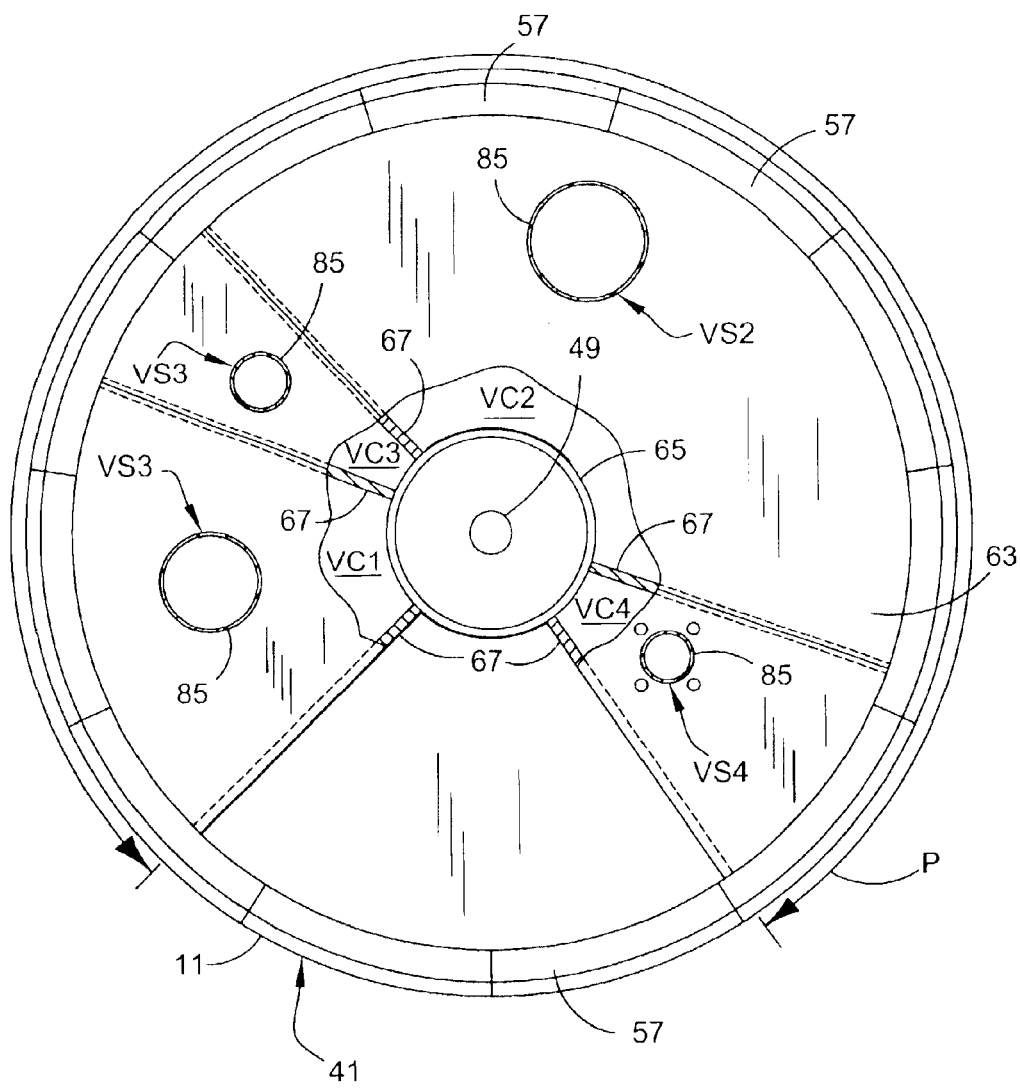
FIG. 6 is a schematic side elevation of the forming drum with portions broken away to show interior construction.

As illustrated in FIG. 6, the four vacuum sources VS1–VS4 comprise a plurality of vacuum chambers VC1, VC2, VC3 and VC4, respectively, on the inside of the drum 41 extending over respective arcuate segments of the aforementioned forming path P. The vacuum chambers VC1–VC4 are defined by structure comprising, in one embodiment (FIGS. 3–6), a pair of spaced apart side walls 63 extending generally parallel to the drum wall 43 on the inside of the drum 41, a cylindric central hub 65 connecting the side walls 63, and a series of radial partitions or dividers 67 between the side walls extending radially from the central hub 65 to adjacent the rim 45 of the drum and forming the end walls of the chambers VC1–VC4. Each vacuum chamber has an arcuate, elongate entrance opening 71 (FIGS. 3 and 4) underlying the rim 45 of the drum 41 and a corresponding arcuate segment of the forming path P. Each vacuum chamber communicates with the foraminous forming surface 11 moving along that segment of the path P via the openings 47 in the rim 45 of the drum. To provide an air resistant seal between the rim 45 and the entrance openings 71 of the vacuum chambers VC1–VC4, rim seals 75 are mounted on the inward-facing surface of the rim 45 for sliding, sealing engagement with the side walls 63 of the vacuum chambers VC1–VC4. Seals (not shown) are also mounted on the partitions or end walls 67 for sliding, sealing engagement with the inward-facing surface of the rim 45. The seals may be formed of a suitable material such as felt to permit the sliding, sealing engagements. The structure defining the vacuum chambers VC1–VC4 is supported in a stationary position by one or more braces 79 mounted on a supporting surface 81 (FIG. 3).

In the embodiment shown, the first and third vacuum chambers VC1–VC3 extend along segments of the forming path P corresponding to the first forming chamber 7; the second vacuum chamber VC2 extends along a segment of the forming path P corresponding to the second forming chamber 9; and the fourth vacuum chamber VC4 extends along a segment of the forming path downstream of second forming chamber 9. The absolute and relative lengths of the segments can vary depending on various factors, to be discussed hereinafter.

Each vacuum source VS1–VS4 also includes an air handling mechanism for generating a vacuum in the respective vacuum chamber. In one embodiment, each such mechanism comprises an air duct 85 connected at one end to the vacuum chamber and at its other end to a device or system 87 (e.g., exhaust fan and motor) for generating an air flow out of the vacuum chamber. It is preferable (although not essential) that each air handling mechanism be adjustable to vary the air flow in its respective vacuum chamber independently of the other vacuum chambers, so that the vacuum in each such chamber may be adjusted as needed or desired. Appropriate controls (e.g., dampers, variable speed fans, etc.) for effecting this adjustment are well known in the art and thus will not be described in detail.

The first forming chamber 7 comprises one or more walls 95 configured to define an interior volume to which the forming surface 11 is exposed upon movement of the forming surface within the forming chamber to form the first layer L1 of the article 3. The second forming chamber 9 is similarly constructed to have walls 99 which define an interior volume to which the forming surface 11 is exposed upon movement of the forming surface within the forming chamber to form the second layer L2 of the article 3. The forming chambers 7, 9, are supported by one or more suitable support frames (not shown) which may be anchored and/or joined to other suitable structural components, as necessary or desirable.

In the embodiment shown in FIG. 1, each of the first and second fiber feed mechanisms 21, 35 comprises a conventional source of fibrous material which delivers a fluent fibrous material (e.g., a flow of discrete fibers) into a respective forming chamber 7, 9. The specific fiber feed mechanisms used may vary, depending on various factors, including the type of fiber being introduced into the chamber. Of course, the type of fiber introduced will depend on the desired composition of the layer formed in the chamber. Typically, fibers of different types will be introduced into the first and second chambers 7, 9, but the same type of fiber can be introduced into both chambers, if desired. By way of example, the first fiber feed mechanism 21 may comprise a conventional fiberizer operatively positioned to deliver fibers into the first chamber 7 through a first fiber inlet 101, and the second fiber feed mechanism 35 may comprise a conventional rotary hammer mill or rotatable picker roll operatively positioned to deliver fibers into the second chamber 9 through a second fiber inlet 105. However, it is to be understood that fluent fibrous material may be delivered to the interiors of the forming chambers 7, 9 in other ways by other suitable devices (e.g., unbailing systems, carding systems, reclaiming systems and other bulk dispensing mechanisms such as those available from Fibercontrols, a business having offices in Gastonia, N.C.) without departing from scope of this invention. As an example, suitable fiberizers and/or hammer mills are available from Paper Converting Machine Company, a business having offices located in Green Bay, Wis., U.S.A.

The fibrous material may include natural fibers, synthetic fibers and combinations thereof. Examples of natural fibers include cellulosic fibers (e.g., wood pulp fibers), cotton fibers, wool fibers, silk fibers and the like, as well as combinations thereof. Synthetic fibers can include rayon fibers, polyolefin fibers, polyester fibers and the like, and combinations thereof. The fibrous materials employed in the apparatus of FIG. 1 may be derived, for example, from batts B of fibers fed to the fiber feed mechanisms 21, 35 where the batts are converted into discrete fibers and delivered through the fiber inlets 101, 105 of the forming chambers 7, 9.

Each of the first and second superabsorbent material (SAM) feed mechanisms 25, 37 comprises a conventional source of SAM which delivers the fluent material into a respective forming chamber 7, 9. For example, particles or fibers of superabsorbent material may be introduced into the forming chambers by employing conventional mechanisms such as pipes, channels, spreaders, nozzles and the like, as well as combinations thereof. In the illustrated embodiment, superabsorbent material is delivered into the first forming chamber 7 by a delivery conduit and nozzle system (which is shown schematically in FIG. 1 and indicated at 25), and superabsorbent material is delivered into the second forming chamber 9 by a delivery conduit and nozzle system (also shown schematically in FIG. 1 and indicated at 37). Typically, different superabsorbent materials will be introduced into the first and second chambers, but the same materials can be introduced into both chambers, if desired. Superabsorbent materials are well known in the art, and are readily available from various suppliers. For example, FAVOR SXM 880 superabsorbent is available from Stockhausen, Inc., a business having offices located in Greensboro, N.C., U.S.A.; and DRYTECH 2035 is available from Dow Chemical Company, a business having offices located in Midland, Mich., U.S.A.

Examples of techniques for introducing a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

The fibers, particles and other desired material may be entrained in any suitable fluid medium within the forming chambers 7, 9. Accordingly, any reference herein to air as being the entraining medium should be understood to be a general reference which encompasses any other operative entraining fluid.

The use of two independent forming chambers 7, 9, independent fiber feed mechanisms 21, 35 and SAM feed mechanisms 25, 37 allows independent control over the composition and configuration of the first and second layers being formed. The extent or reach of each forming chamber 7, 9 along the arcuate forming path P is determined by the desired mass flow or basis weight (g/m$^2$) within each of the first and second layers L1, L2 and by the so-called "clean-wire" effect, which is the tendency of fibers and other materials to build up on the foraminous forming surface 11 more quickly toward the beginning of the forming path P. As the forming surface 11 (e.g., wire screen) enters the first forming chamber 7, the foraminous forming areas 61 are empty or clean and thus there is very little resistance to the flow of air through these areas. As a result, the initial rate of material build-up on the forming surface is relatively fast. However, as the thickness of material deposited on the surface increases, the rate of air flow and material build-up decreases. Consequently, the length of the first forming chamber 7 and its matching vacuum chambers (e.g., first and third vacuum chambers VC1, VC3) can be significantly smaller than the length of the second forming chamber 9 (and any later chambers). By way of example, the first forming chamber 7 is preferably 10% to 75% of the total forming chamber length along forming path P, more preferably 10% to 60% of the total forming chamber length, and even more preferably 10% to 50% of the total forming chamber length. Actual forming lengths of the chambers 7, 9 are determined by air flow requirements of the fiber feed mechanisms 21, 35.

In the embodiment shown in FIG. 1, the forming length of the first forming chamber 7 represents approximately 20–30% of the total outer circumference of the drum 41 and corresponds to an angle of about 90 degrees, for example, and the forming length of the second forming chamber 9 represents approximately 33–50% of the total outer circumference of the drum 7 and corresponds to an angle of about 150 degrees, for example.

Figure 2:
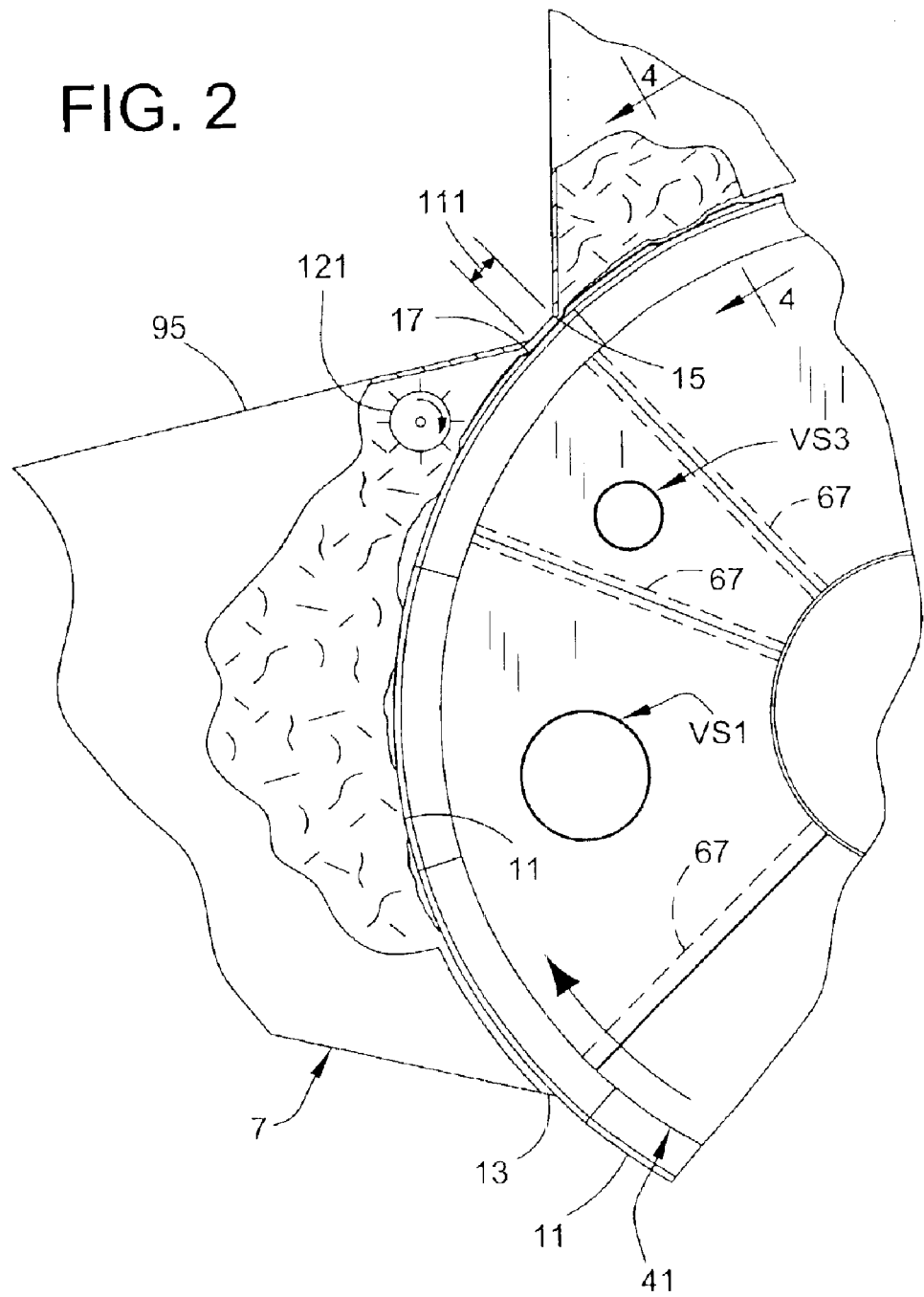
FIG. 2 is an enlarged side elevation of a portion of the apparatus of FIG. 1 with parts broken away to show details.

To prevent any substantial commingling of the fibers and superabsorbent materials in the respective forming chambers 7, 9, and to prevent air leakage from one forming chamber to another chamber, it is preferable that the first and second forming chambers be substantially discrete or separate. As used in this context, "substantially" means that any connecting space or passage between the two chambers should have a cross sectional area taken in any plane generally perpendicular to the forming surface 11 no greater than about 200 cm$^2$ (31 in$^2$), and more preferably no greater about 100 cm$^2$ (15 in$^2$), thus avoiding any substantial flow air between the chambers. Even more preferably, the first and second chambers 7, 9 are separated from one another by a zone of separation 111 along the forming path P (see FIG. 2). The length of this zone 111 should be minimized, if possible, so as not to significantly reduce the forming areas within the forming chambers. In this regard, the zone of separation 111 is preferably in the range of 1% to 25% of overall length of the forming path P, more preferably in the range of 1% to 15% of such overall length, and even more preferably in the range of 1% to 5% of the overall length of the forming path P.

In the embodiment of FIG. 1, the foraminous forming surface 11 travels through the zone of separation 111 after it exits the first forming chamber 7 and before it enters the second forming chamber 9. As illustrated, the forming path P in this zone is open to atmosphere and free of enclosure. However, it will be understood that this area could be enclosed in a suitable housing which may be separate from the forming chambers 7, 9 or an integral part of one or both forming chambers. Suitable sealing devices (not shown) are provided at the entrances 13, 15 and exits 17, 19 of the forming chambers for inhibiting the leakage and/or commingling of air, fibers and/or superabsorbent materials from the two forming chambers. Such devices may include sealing rolls, sealing strips, or other conventional devices well known in the art.

The apparatus 1 also includes a first removing and directing mechanism 121 for removing a portion of the first layer L1 and directing the portion removed back into the first forming chamber 7. In the preferred embodiment, this mechanism comprises a rotatable scarfing roll (also designated 121) mounted adjacent the forming path P, generally toward the exit 17 of the first forming chamber 7. The roll 121 is operatively connected and joined to a suitable shaft member (not shown), and is driven by a suitable drive system (not shown). The drive system may include any conventional apparatus, such as a dedicated motor, or a coupling, gear or other transmission mechanism operatively connected to the motor or drive mechanism used to rotate the forming drum 7.

The scarfing roll 121 (or other removal mechanism) has a cutting or abrasive surface suitable for removing material, and it is spaced from the forming surface 11 a distance generally corresponding to the desired thickness T1 (FIGS. 7–9) of the first layer L1 above the forming surface in the Z direction. Upon rotation, the scarfing roll 121 contacts the upper surface of the first layer L1 (i.e., the surface away from the forming surface 11) and removes any material beyond the desired thickness, thereby leveling the first layer prior to its entry into the second forming chamber 9. The rotational speed of the scarfing roll 121 should be suitably selected to provide an effective scarfing action against the contacted surface of the layer. In like manner, any other suitable trimming mechanism may be employed in place of the scarfing roll to provide a cutting or abrading action to the fibrous layer L1 by relative movement between the absorbent member and the selected trimming mechanism.

The spacing between the scarfing roll 121 and the forming surface 11 is preferably adjustable in conventional fashion, so that the thickness T1 of the first layer L1 in the Z direction can be varied, as desired. It is also preferable that the material removed be directed back into the first forming chamber 7 to preserve mass flow, meaning that all of the material, including fibers and superabsorbent materials, delivered to the first chamber are used to form the first layer. This allows the basis weight of the first layer formed in the first forming chamber to be closely controlled. This closed loop mass flow system can be achieved in different ways.

Figure 1A:
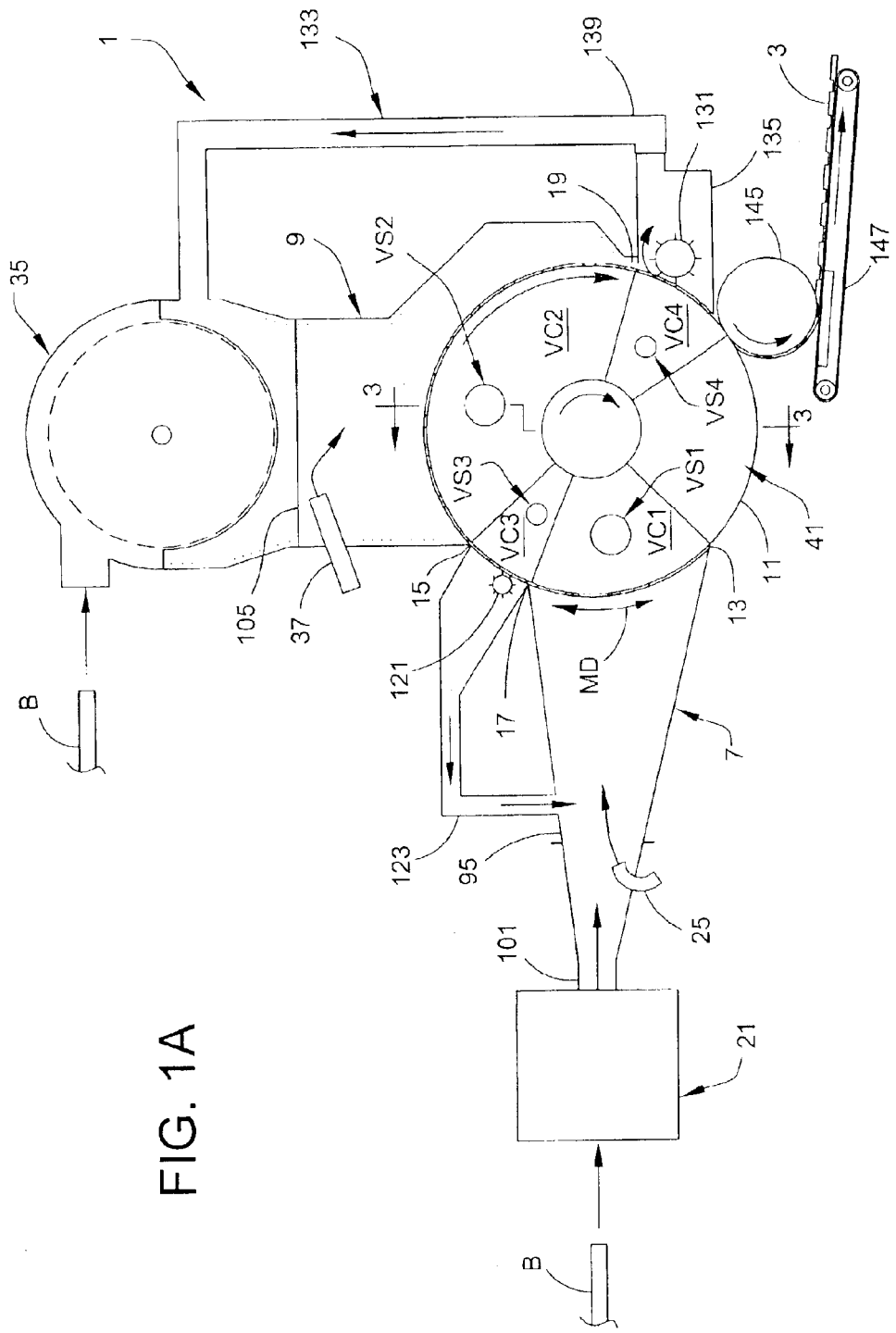
FIG. 1A is a view similar to FIG. 1 but showing a second embodiment of the apparatus.

As shown in FIG. 1, for example, the removing and directing mechanism 121 is located inside the forming chamber 7 generally toward the exit 17 of the chamber and functions to throw or "kick back" the removed material into the forming chamber so that it can be redeposited on the forming surface 11. If a rotary mechanism such as the scarfing roll 121 is used to trim layer L1, it is preferable that the mechanism rotate in a direction counter to the direction of movement of the forming surface so that the removed material is directed back in a direction away from the exit 17 of the chamber 7. Alternatively, the removing and directing mechanism 121 can be located outside the forming chamber 7 and include a suitable conveyor 123 for returning the removed material back to the first chamber (see FIG. 1A). For example, a vacuum source such as a fan can be implemented to pneumatically convey the removed material back to the forming chamber directly or to the fiber feed mechanism 21 for re-introduction into the forming chamber 7.

Figure 7:
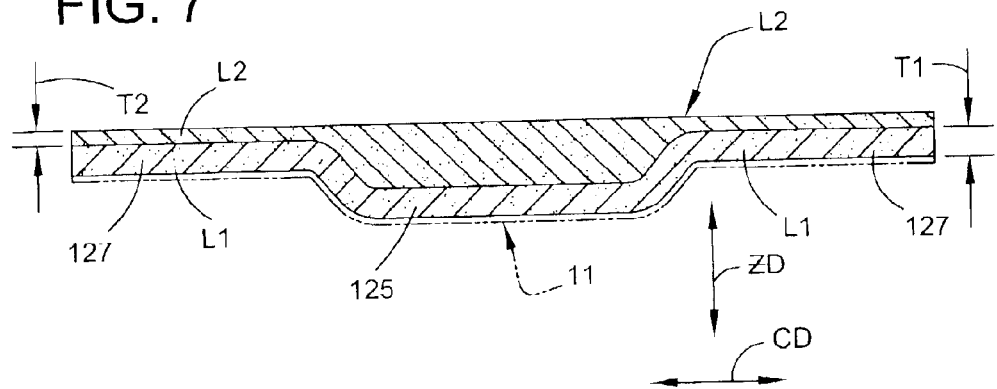
FIGS. 7–9 are sectional views showing variations in the layers of an article formed by the apparatus of FIG. 1.
Figure 8:
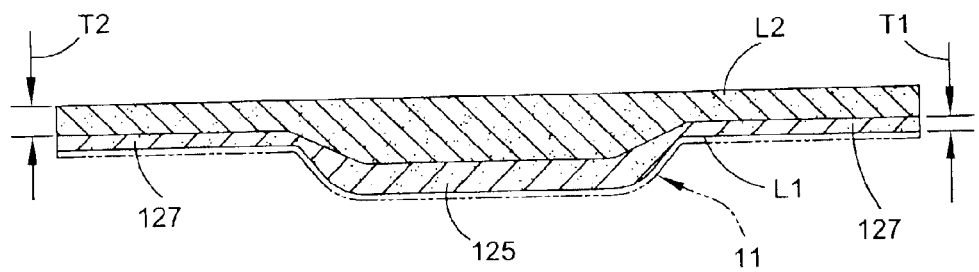
Figure 9:
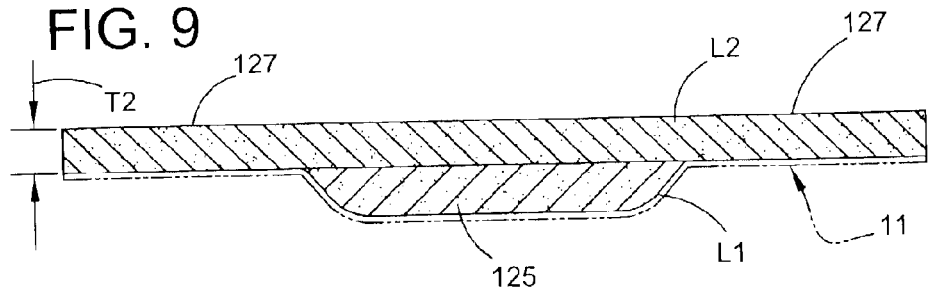

The removing and directing mechanism 121 described above allows the distribution of material in the first layer L1 to be closely controlled in the cross-machine and Z directions CD, ZD. Examples of different distribution patterns are shown in FIGS. 7–9, which illustrate variations of a two-layer absorbent article 3 having a central liquid holding formation 125 over the second (pocket) section 61B of a respective forming area 61 and a pair of ears 127 extending laterally from the central formation over the first section 61A of the forming area. FIG. 7 shows a variation where the gap between the removal mechanism (e.g., scarfing roll 121) and the forming surface has been set to be relatively large (e.g., 0.025 in.) so that only a small amount of material is removed from the first layer L1. As a result, the first layer L1 has a width in the cross-machine direction CD corresponding to the full width of the two-layer article and a relatively large generally uniform thickness (e.g., 0.25 in.) in the Z direction ZD across the entire width of the first and second sections 61A, 61B of the forming area 61. FIG. 8 shows a variation where the gap between the removal mechanism 121 and the forming surface 11 has been reduced (e.g., to 0.125 in.) so that a moderate amount of material is removed from the first layer L1. Consequently, the layer has the same width as FIG. 7 but a reduced thickness T1 (e.g., 0.125 in.) in the Z direction across the first section 61A of the forming area at the ears 127 and an increased thickness across the second (pocket) section 61B in the area of the central formation 125. FIG. 9 shows a variation where the gap between the removal mechanism 121 and the forming surface 11 has been substantially eliminated so that a heavy amount of material is removed from the first layer L1. As a result, the layer L1 is completely removed in the first section 61A of the forming area at the ears 127 and has an even greater thickness in the Z direction across the second (pocket) section 61B at the central formation 125. In this case, a mechanism 121 such as a brush roll should be used to avoid damage to the forming surface 11. Note that as more and more material is removed from layer L1 across the first section 61A of the forming area 61 at the ears 127, the mass distribution of the first layer L1 becomes more and more concentrated across the pocket section 61B at the central formation 125 so that the thickness in this area in the Z direction increases. Thus, the closed-loop mass flow system of the present invention allows close control over the mass distribution of the first layer L1.

Referring again to FIG. 1, a second removing and directing mechanism, generally designated 131, is provided for removing a portion of the second layer L2 and directing the portion removed back into the second forming chamber 9. Thus, like the first removing and directing mechanism 121, the second mechanism 131 is a closed-loop mass flow system and it has the same advantages discussed above regarding the first removing and directing mechanism. In the embodiment illustrated in FIG. 1, the mechanism 131 comprises a scarfing roll mounted immediately downstream of the exit 19 of the second forming chamber 9. Like the scarfing roll 121 previously described, the second scarfing roll 131 has a cutting or abrasive surface suitable for removing material from the second layer L2, and the roll is spaced from the forming surface 11 a distance generally corresponding to the desired combined thicknesses T1, T2 of the first and second layers above the forming surface in the Z direction (see FIGS. 7–9). Upon rotation, the roll 131 contacts the upper surface of the second layer L2 (i.e., the surface away from the foraminous forming surface 11) and removes any material beyond the desired thickness. Devices other than a scarfing roll may be used to remove this excess material from the second layer. The second removing and directing mechanism 131 also includes a pneumatic conveyance system 133 comprising, in one embodiment, a housing 135 for the roll and a duct 139 connected to the housing for pneumatically conveying the removed material back to the second forming chamber 9. The air stream in the duct 139 may be generated by an exhaust fan or other suitable means (not shown). Alternatively, the second removing and directing mechanism 131 may be located inside the second forming chamber 9, preferably toward the exit 19 of the chamber, much like the first removing and directing mechanism 121 is located toward the exit 17 of the first forming chamber 7 (see FIG. 1B).

In general, a "kick-back" removal and directing mechanism 121 of the type described above in connection with the first forming chamber 7 is preferred where relatively small amounts of material are to be removed. Where heavier amounts are to be removed, it may be preferable to use a removal and directing mechanism (e.g., 131) which includes a separate conveyance system (e.g., system 133 shown in FIG. 1) for conveying the removed material back to the appropriate forming chamber. For further details regarding exemplary systems, reference may be made to pending U.S. patent application Ser. No. 09/840,384 entitled METHOD AND APPARATUS FOR GEOMETRIC SCARFING by Joseph M. Kugler et al., filed Apr. 23, 2001.

Referring to FIG. 1, the four vacuum chambers VC1–VC4 are arranged so that the first and second chambers VC1, VC2 communicate with the first and second forming chambers 9, 11, respectively. In the illustrated embodiment, the first vacuum chamber VC1 extends along a first arcuate segment from the entrance 13 of the first forming chamber 7 to a location generally upstream of the first removing and directing mechanism 121; the second vacuum chamber VC2 extends along a second arcuate segment from the entrance 15 of the second forming chamber 9 to the exit 19 of the second forming chamber; the third vacuum chamber VC3 extends between the first and second forming chambers 7, 9 along a third arcuate segment from adjacent or upstream of the first removing and directing mechanism 121, past the zone of separation 111 to the entrance 15 of the second forming chamber 9; and the fourth vacuum chamber VC4 extends from the exit 19 of the second forming chamber to a location downstream of the second removing and directing mechanism 131 generally corresponding to a rotatable vacuum transfer cylinder 145 which functions to transfer articles from the drum to a suitable conveyor 147 or other location for further processing of the articles. As described above, the vacuums in the various vacuum chambers VC1–VC4 are preferably capable of independent adjustment so that the degree of vacuum in each chamber can be independently varied as needed. By way of example, the vacuums in the first and second vacuum chambers VC1, VC2 should be sufficient (e.g., in the range of from −20 to −30 in. water) to produce first and second layers L1, L2 of the required thicknesses and mass distributions, and the vacuums in the third and fourth vacuum chambers VC3, VC4 should be sufficient (e.g., in the range of from −15 to −20 in. water) to hold the materials on the forming surface 11 as material is removed by the removing and directing mechanisms 121, 131. The interior space of the drum between the fourth and first vacuum chambers is preferably not under vacuum optionally, the fourth vacuum chamber could be divided into two sections, the first section being located on the arcuate segment of drum corresponding to the removing and directing mechanism 131 and the second section being located downstream from the first generally in the area of the transfer cylinder 145. In this configuration, the vacuum in the second section preferably would be less (e.g., −5 to −7 in. water) than the vacuum in the first section to facilitate transfer of the articles 3 from the drum to the cylinder.

In operation, the air handling mechanisms 87 are operated to establish vacuums of appropriate magnitude in respective vacuum chambers VC1–VC4 to create air flows through the forming surface 11. Further, the first and second fiber feed mechanisms 21, 35 and first and second superabsorbent material feed mechanisms 25, 37 are operated to introduce selected fibers and selected superabsorbent materials into respective first and second chambers 7, 9 at the desired rates to form the first and second layers L1, L2 of the articles 3 to be made. (Additional forming chambers and associated equipment can be provided to form additional layers, if desired.) The gaps between the scarfing rolls 121, 123 and the forming surface 11 are also adjusted to provide the desired thicknesses and contours.

As the forming surface 11 enters and then moves through the first forming chamber 7 along the forming path P toward the exit of the chamber 17, the fluidized fibers and superabsorbent materials within the forming chamber are operatively carried or transported by an entraining air stream and drawn inward by the vacuum toward the forming surface 11. Air passes inward through the foraminous areas 61 of the surface 11 and is subsequently passed out of the drum 41 through the vacuum ducts 85. Fibers and other particulates are collected by the forming surface 11 as the air passes therethrough such that the collection of fibrous material forms a first layer L1 of material on the foraminous areas 61 of the forming surface. As the layer passes the first removal and directing mechanism (e.g., the first scarfing roll 121), excess thickness of the layer L1 is trimmed and removed to an extent determined by the gap between the removal mechanism and the forming surface 11. The removed material is returned to the first forming chamber 7 either directly by "kick-back" or by a separate return system as previously discussed.

Subsequently, the drum 41 carrying the trimmed first layer L1 exits the first forming chamber 7, passes through the separation zone 111 and enters the second forming chamber 9 where the fibers and superabsorbent material in the chamber are vacuum drawn toward the forming surface and deposited on the first layer L1 to form the second layer L2. As they are deposited, the fibrous material of the second layer becomes entangled and otherwise commingles with the fibrous material of the first layer, thereby improving fluid transfer between the layers. Further, because the two forming chambers are independent, the first and second layers L1, L2 are always in proper phase (registration) with one another. After exiting the second forming chamber 7, the forming surface 11 passes beneath the second scarfing roll 131 which functions to remove or trim any excess portions of the second layer L2, as needed. The removed material is conveyed back to the second forming chamber 9 by the pneumatic conveyance system 133.

Following the second scarfing operation, the forming surface 11 on which the two-layer articles 3 are formed moves to a release zone of the apparatus 1 disposed exterior of the forming chambers. In the release zone, the articles are transferred by the vacuum transfer cylinder onto the conveyor 147, which may be a vacuum conveyor for facilitating the transfer to the conveyor. Alternatively, the articles 3 may be transferred directly to the conveyor without an intervening transfer cylinder. The release of the articles 3 can be assisted by the application of air pressure from the interior of the drum 41. The conveyor 147 receives the formed articles 3 and conveys the them to a collection area or to a location for further processing (not shown). Suitable conveyors can, for example, include conveyer belts, vacuum drums, transport rollers, electromagnetic suspension conveyors, fluid suspension conveyors or the like, as well as combinations thereof. Removal of the articles 3 from the forming surface 11 can alternatively be accomplished by the weight of the articles, by centrifugal force, by mechanical ejection, by positive air pressure or by some combination thereof or by another suitable method without departing from the scope of this invention. As an example, the removed articles 3 of the illustrated embodiment are interconnected as a series of articles, each of which has a selected surface contour that substantially matches the contours provided by the corresponding foraminous areas 61 of the forming surface 11 upon which the articles are formed.

It will be readily apparent that various conventional devices and techniques can be employed to further process the articles after removal from the drum 41. For example, the articles can be compressed at a debulking station. In addition, various conventional devices and techniques can be employed to sever the articles 3 into predetermined lengths to provide selected air formed fibrous absorbent members for example. The severing system may, for example, include a die cutter, a water cutter, rotary knives, reciprocating knives, energy beam cutters, particle beam cutters or the like, as well as combinations thereof. After severing, the discrete articles 3 can be transported and delivered for further processing operations, as desired.

The apparatus and process described above are effective for the manufacture of multiple-layer fibrous articles while maintaining close control of the fiber and SAM concentrations within each layer, and while providing consistent weight variability to the finished articles. The flexibility of the system allows the mass flow rate of fibrous material and superabsorbent material (if used) to be varied between forming chambers. For example, fibrous materials may be introduced into the first and second forming chambers at first and second mass flow rates, respectively, with the first rate being greater than or less than the second rate. Similarly, superabsorbent materials may be introduced into the first and second forming chambers at first and second mass flow rates, respectively, with the first rate being greater than or less than the second rate. The single-drum, multiple forming chamber system disclosed herein is more economical than two or more independent forming systems and eliminates the possibility of "out-of-phase" defects and waste associated with such independent systems. The teachings of the present invention may also facilitate the retrofitting of a single forming system into a multiple forming system by nature of its favorable space requirements, thus allowing the manufacturing conversion to take place in less time and for less capital.

The product benefits of the process of the present invention include the capability of achieving any SAM mixing distribution desired, including homogeneous, layered or stratified. Further, the SAM distributions can be similar or different between layers. This flexibility allows for product enhancements such as a dedicated fluid intake and fluid distribution layers. Using multiple SAMS and/or multiple fibers can also be beneficial from a grade cost standpoint because high performance and high cost materials can be deployed more judiciously.

Figure 10:
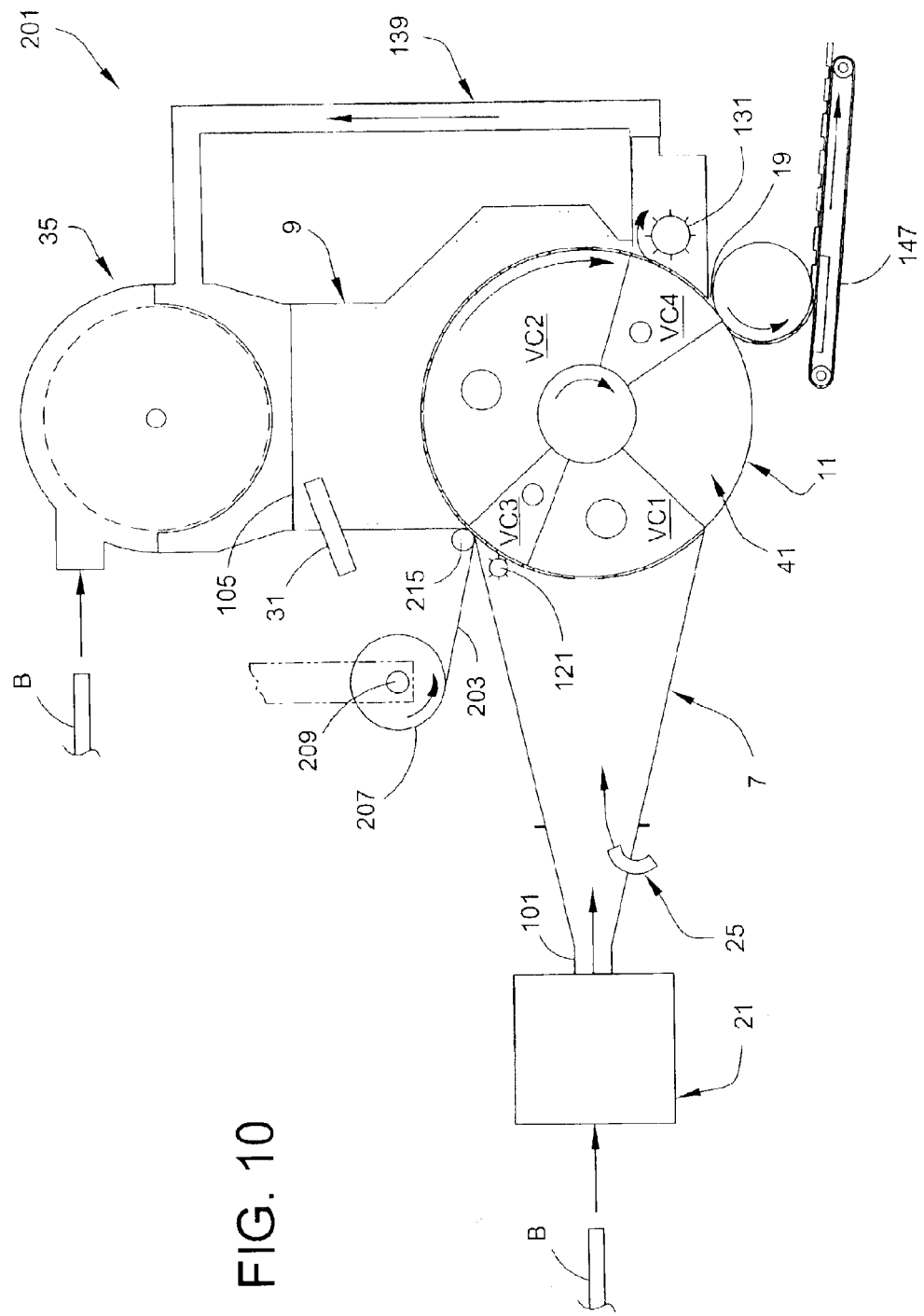
FIG. 10 is a view similar to FIG. 1 but showing apparatus for incorporating a reinforcing web in the articles made by the apparatus.
Figure 11:
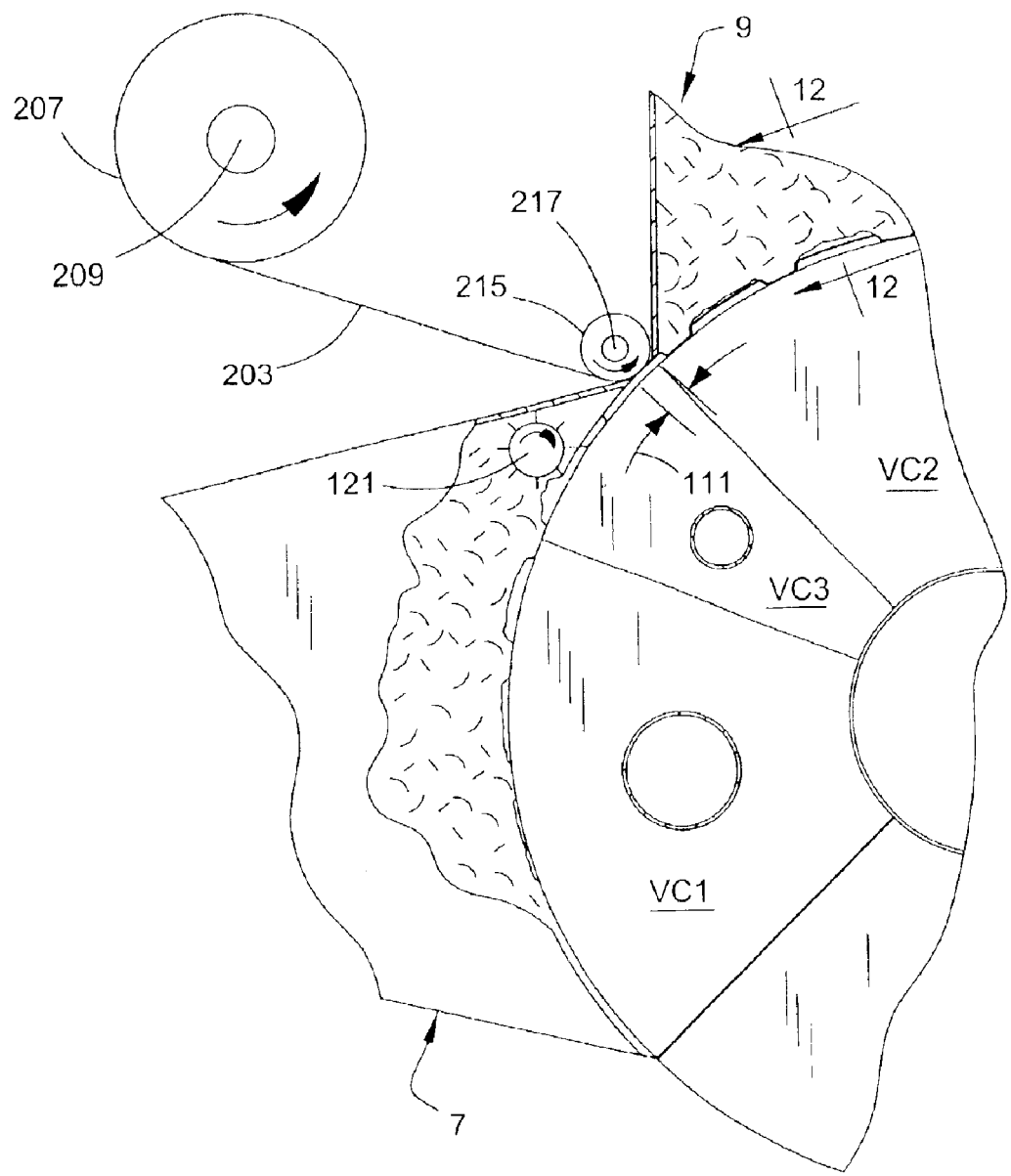
FIG. 11 is an enlarged side elevation of a portion of the apparatus of FIG. 10 with parts broken away to show details.
Figure 12:
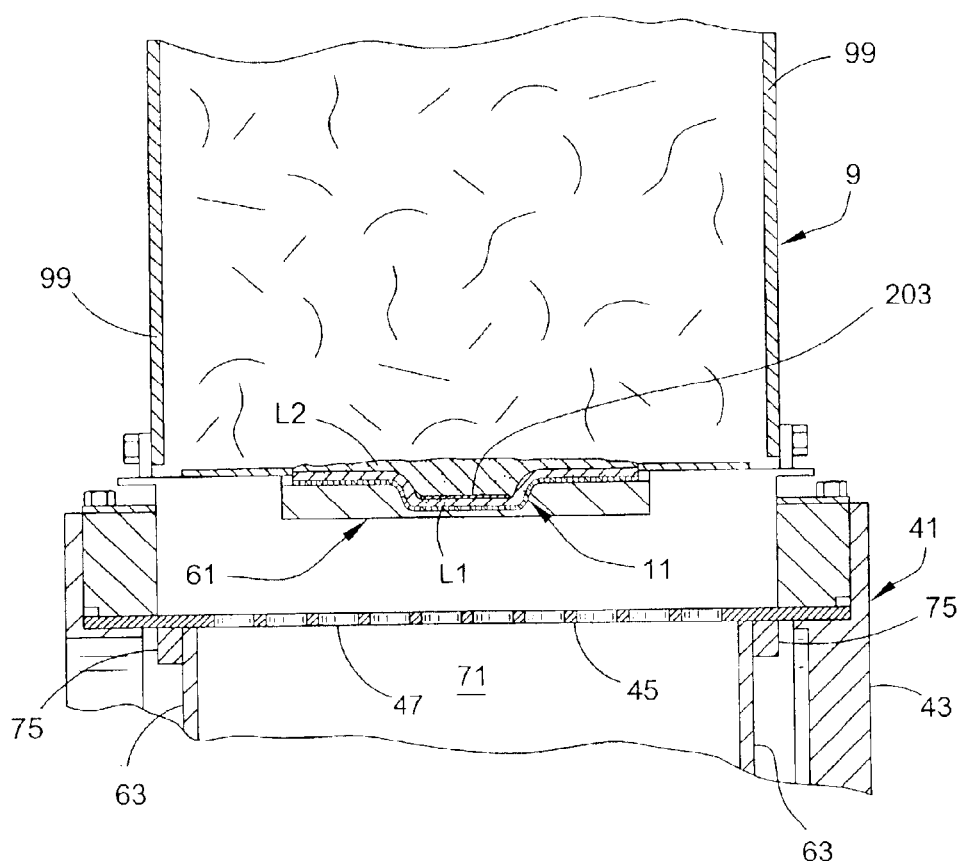
FIG. 12 is an enlarged sectional view taken in the plane of 12—12 of FIG. 11.
Figure 13:
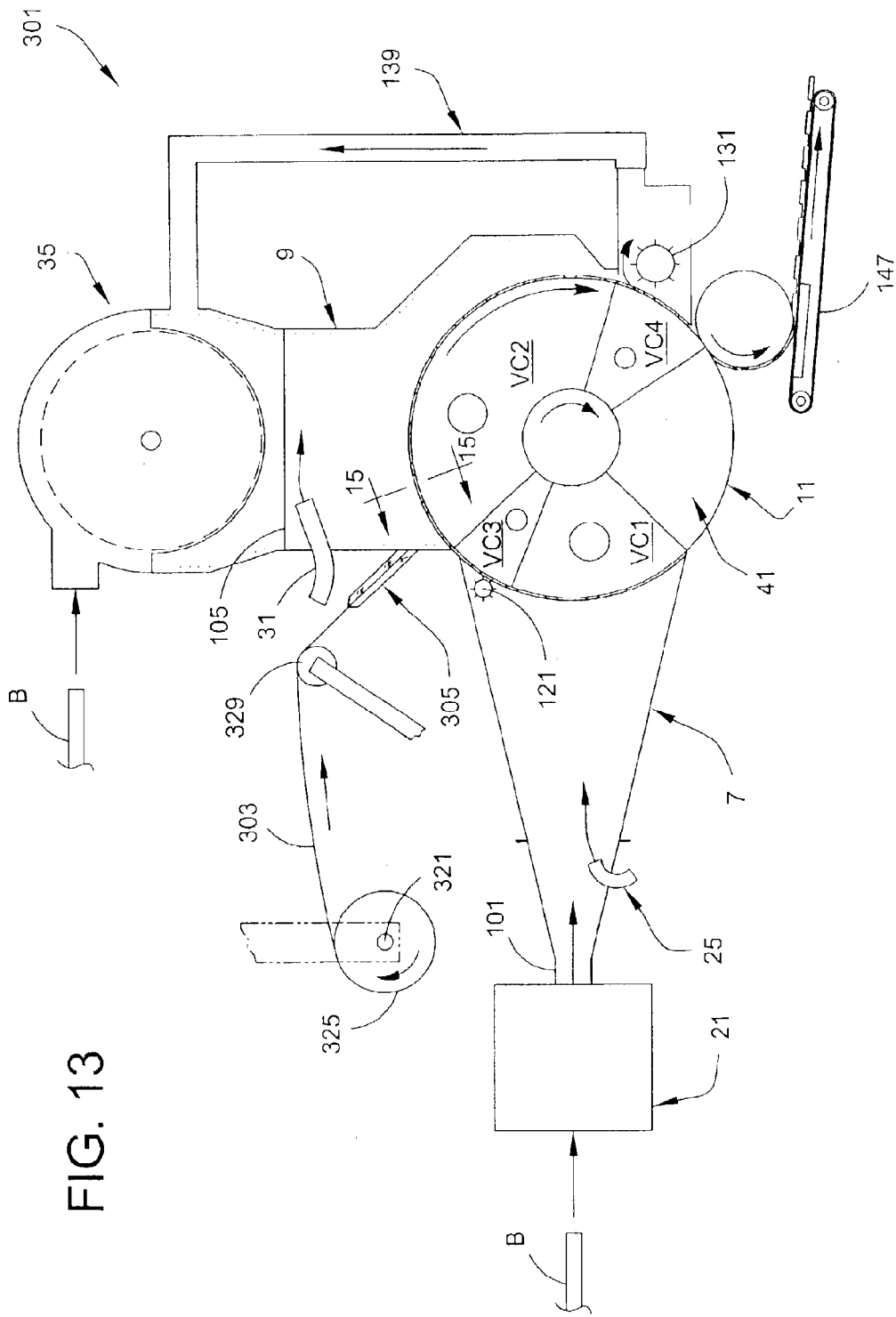
FIG. 13 is a view showing a modification of the apparatus of FIG. 10.

FIGS. 10–12 illustrate apparatus, generally designated 201, substantially similar to apparatus 1 described above, and corresponding parts are designated by the same reference numbers. The main difference is that the apparatus 201 is operable to add a web 203 of reinforcing material to the articles, preferably (but not necessarily) at a location between the first and second layers L1, L2, or between any two layers of an article comprising more than two layers.

In the embodiment illustrated in FIGS. 10 and 11, the reinforcing web is a continuous strip of material that is fed from a source, such as a supply roll 207 mounted on a conventional unwind mechanism 209, for application of the web to the upper face of the first layer L1 as it moves through the zone of separation 111 between the first and second chambers 7, 9. Application of the web 203 to material collected on the forming surface 11 is facilitated by a suitable delivery mechanism such as a guide roll 215 mounted adjacent the forming surface 11. The guide roll is rotatable on a shaft 217 which is preferably driven by suitable means at the same speed as the forming surface 11. The roll functions to guide the web so that it is overlaid on layer L1 in a position in which it is properly located in the cross-machine direction CD and Z direction ZD relative to the articles being formed.

The reinforcing web 203 is desirably constructed of a material that is sufficiently porous to permit entraining air flowing within the second forming chamber 9 toward the forming surface 11 to pass therethrough. Even more desirably, the reinforcing web is at least semi-permeable to the discrete fibers flowing within the forming chamber 9. For example, the reinforcing web 203 of the illustrated embodiment may be a scrim (e.g., netting or mesh material) formed from longitudinally (e.g., machine direction MD) and laterally (e.g., cross-machine direction CD) oriented filaments arranged in a generally grid pattern and interconnected such as by being bonded at intersecting points to form an open mesh (e.g., having a plurality of generally rectangular or square-shaped openings) through which the fluent fibrous material in the forming chamber 9 may permeate. Alternatively, the scrim filaments may be oriented other than in a longitudinal or lateral orientation so as to define openings which are other than rectangular or square-shaped, such as diamond shaped, triangular shaped or other suitably shaped openings.

In one embodiment, the openings defined by the filaments of the scrim are sufficiently sized relative to the discrete fibers flowing within the second forming chamber 9 to facilitate entanglement of fibers with the scrim upon entry of the scrim into the forming chamber. As an example, the longitudinally oriented filaments are laterally spaced from each other a distance of about 2 mm to about 30 mm and the laterally oriented filaments are spaced from each other a distance of about 2 mm to about 30 mm. The width of the scrim is desirably about 25 percent to about 100 percent of the width of the absorbent member 3, more desirably about 25 percent to about 75 percent, and even more desirably about 50 percent to about 75 percent. As a further example, the width of the scrim may be in the range of about 20 mm to about 400 mm.

The scrim filaments can be constructed of a transparent, or at least translucent, material so as to be generally invisible when a fibrous article 3 incorporating the scrim is incorporated into an article such as a diaper, training pants, etc. The scrim may optionally be white so as to be generally invisible but still optically detectable by suitable detection apparatus, or it may be colored for visibility to the consumer. The scrim is often formed with the laterally oriented filaments projecting laterally out beyond the outermost longitudinally oriented filaments. However, it is understood that the scrim may be laterally bounded by the outermost longitudinally oriented filaments without departing from the scope of this invention. It is also contemplated that the reinforcing web may instead comprise an apertured or perforated film, an air permeable woven or non-woven web, or another suitable material without departing from the scope of this invention.

Upon further movement of the forming surface 11 within the second forming chamber 9 toward the exit 19, additional fibrous material is drawn toward the forming surface and collects on the partially formed articles 3 and reinforcing web 203 to further increase the thickness of the articles and to enclose or otherwise secure the reinforcing web therein. Where the reinforcing web 203 is scrim as in the illustrated embodiment or is otherwise at least semi-permeable to the fluent fibrous material, the additional fibrous material collects within and becomes entangled with the reinforcing web and/or with the fibrous material previously entangled with the web, to further secure the web within the articles 3. The entanglement of the fibrous material is desirably sufficient such that the scrim cannot be removed from the fibrous article 3 without fibrous material being removed along with the scrim.

The Z-direction ZD position of the reinforcing web 203 within the thickness of the article 3 is generally a function of where the web 203 is applied to the partially formed article along the forming path P of the forming surface 5 and how the fibers of the first layer L1 are distributed across the forming surface 11 as a result of the operation of the first removing and directing mechanism, as explained above and exemplified in FIGS. 7–9. In general, it is preferred that the web 203 be located generally centrally of the article in the Z direction to minimize any risk that the web will be contacted by the second removing and directed mechanism (e.g., the second scarfing roll 131), since any such contact could result in jamming of the pneumatic conveyance system 133 and/or the second forming chamber 9. To prevent any such jamming, a suitable mechanism (e.g., a trim chopper, not shown) may be installed between the second scarfing roll 131 and the fan of the pneumatic conveyance system 133 for shredding any such scrim material. Preferably, the ZD position of the web 203 at any given location on the article as measured from the upper surface 225 of the second layer L2 (see FIGS. 7–9) is preferably in the range of from about 5 to 95% of the thickness of the article at such location, more preferably in the range of about 7–90%, and most preferably in the range of about 10–75%. It will be understood in this regard that the thickness of the article may vary depending on location. In areas of greater thickness, the preferred spacing of the web 203 below the upper surface 225 of the second layer L2 will be toward the lower limits of the ranges given above. In areas of lesser thickness, on the other hand, the preferred spacing will be more toward the upper limits of the ranges given above. In any event, the spacing should be such as to avoid interference with the second removal and directing mechanism 131.

For reasons to be discussed, it is desired that the web 203 be applied at a location along the forming path P corresponding to the zone of separation 111 so that the web is positioned between the first and second layers L1, L2. However, it will be understood that the web can be applied at other locations along the forming path P, including inside the first forming chamber 7 or inside the second forming chamber 9. In general, the web is desirably applied at a position which corresponds to a location along the path P downstream of the first forming chamber entrance 13 a distance in the range of about 5% to about 66% of the total length of the path P and more desirably in the range of about 5% to about 50%. Where the foraminous area 61 of the forming member 57 has a variable depth to form an article 3 having a variable thickness, the web is even more desirably applied a distance in the range of about 10% to about 40% of the total length of the path P so as to position the reinforcing web 203 generally centrally within the thickness (e.g., in the Z-direction) of the article 3, preferably within the ranges discussed above. For an article 3 of generally uniform thickness, the web 203 is preferably applied a distance in the range of about 30% to about 40% of the total length of the path P. It is understood, however, that the reinforcing web 203 may be applied generally anywhere along the forming path P of the forming surface 11 to locate the web at generally any Z-direction position within the thickness of the article 3, as long as the web is positioned within the article so as to not interfere with operation of the second scarfing roll 131. As noted above, the Z-direction position of the web 203 is also controlled by the mass distribution of layer L1 across the forming surface 11, as exemplified in FIGS. 7–9.

FIGS. 13–16 illustrate apparatus of the present invention, generally designated 301, similar to those described above. (For convenience, corresponding parts are designated by the same reference numbers.) However, in this embodiment the reinforcing web 303 (which has the same characteristics and properties as web 203 described above) is applied to the forming surface 11 in one of the forming chambers. In the illustrated embodiment, the web is introduced into the interior of the second forming chamber 9 for incorporation into the articles 3 by a delivery mechanism comprising a delivery tube, generally indicated at 305. The delivery tube extends through and is supported by a wall 99 of the second forming chamber and has a central passage 309 extending from an inlet end 311 of the tube disposed exterior of the forming chamber 9 to a discharge end 315 disposed within the forming chamber in generally adjacent, radially spaced relationship with the forming surface 11 on which the articles 3 are formed.

The inlet end 311 of the delivery tube 305 is desirably open to the exterior of the second forming chamber 9 for receiving the reinforcing web 303 into the central passage 309 of the tube, and the discharge end 315 is open to the interior of the forming chamber 9 and broadly defines an opening in the forming chamber through which the reinforcing web 303 is introduced into the interior of the forming chamber and exposed to the fluent fibrous material. It is contemplated that the discharge end 315 of the delivery tube 305 may be flush with the wall 99 of the second forming chamber 9 instead of extending into the interior volume thereof, or that the delivery tube may be omitted altogether such that the reinforcing web 303 simply enters the second forming chamber 9 through an opening formed in the wall 99 of the forming chamber, without departing from the scope of this invention. A conventional unwind 321 supports a supply roll 325 of reinforcing web 303 (broadly, a source of reinforcing web) exterior of the forming chamber 9 and an idler roll 329 or other guide mechanism (e.g., an automatic guide system) positioned intermediate the unwind and the inlet end 311 of the delivery tube 305 for guiding the reinforcing web into the tube.

Figure 14:
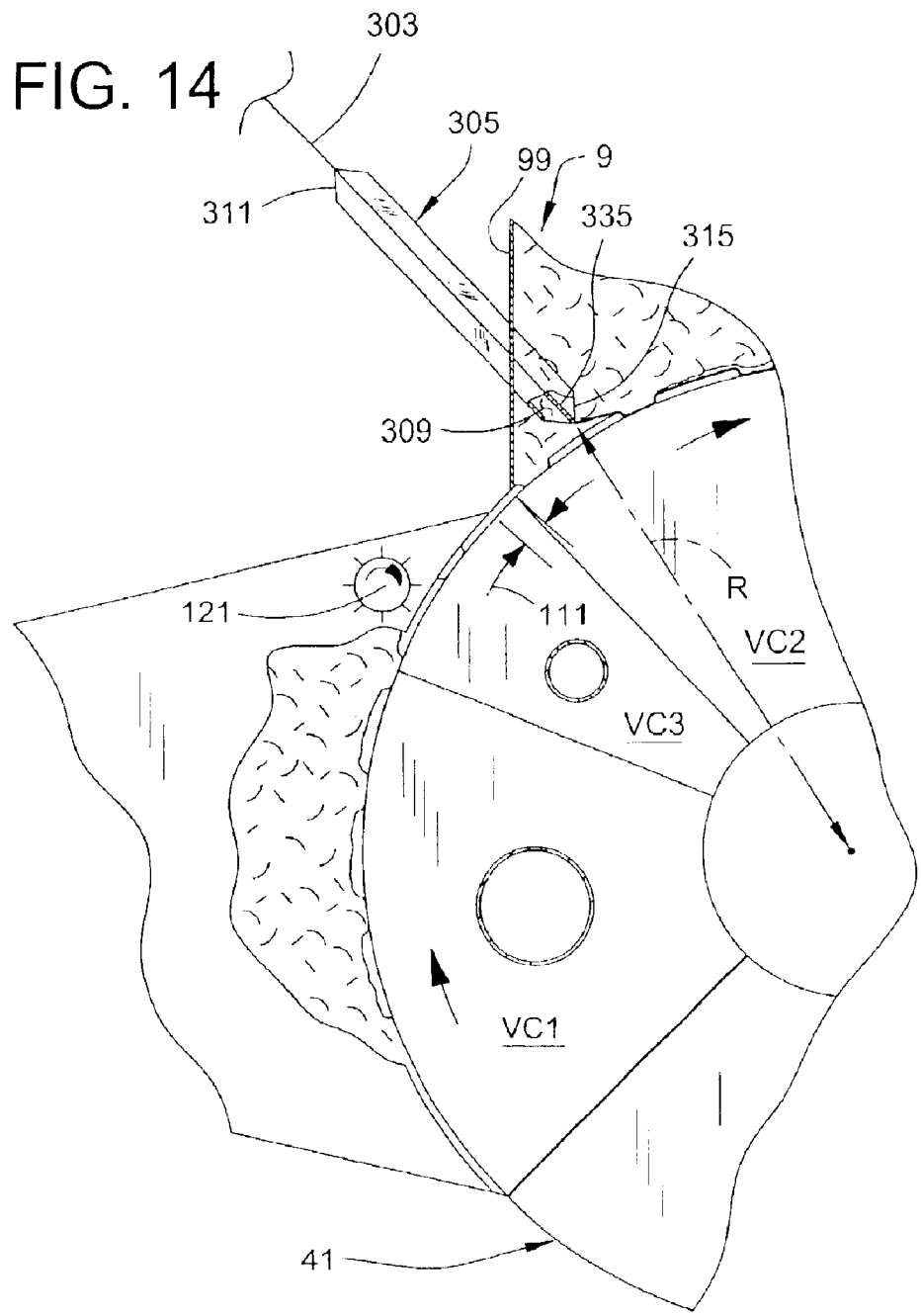
FIG. 14 is an enlarged side elevation of a portion of the apparatus of FIG. 13 with parts broken away to show details.
Figure 15:
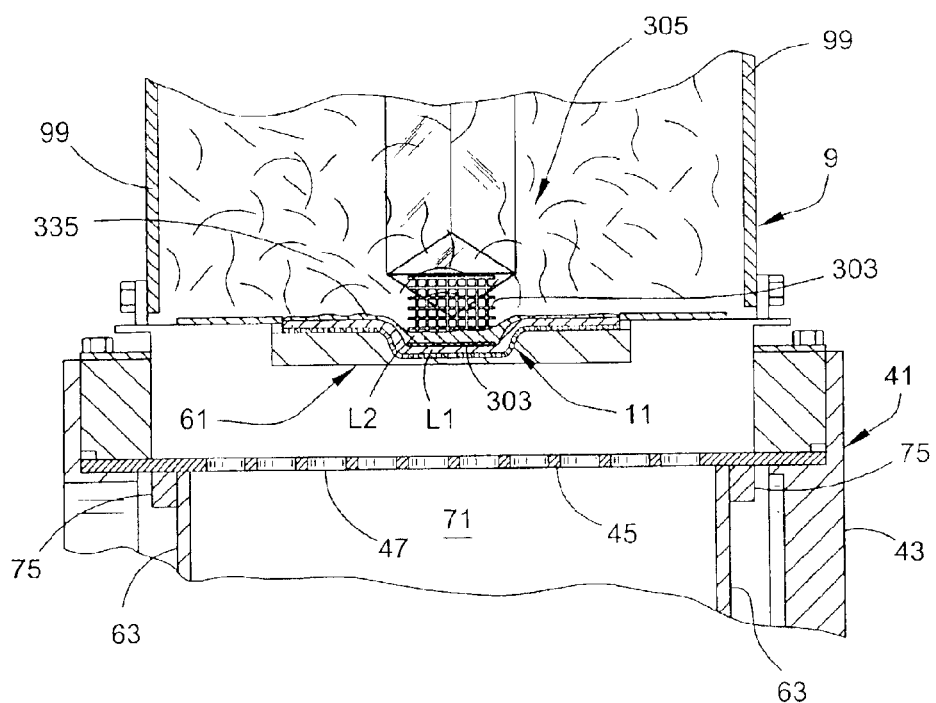
FIG. 15 is an enlarged sectional view taken in the plane of 15—15 of FIG. 13.

As shown in FIG. 14, the delivery tube 305 is desirably oriented to extend longitudinally other than radially relative to the forming drum 41 for reasons which will be described later herein. For example, in the illustrated embodiment the delivery tube 305 is angled downward relative to the wall 99 of the forming chamber 9. Desirably the tube 305 is also oriented such that the longitudinal axis of the tube is oriented at angle in the range of about 90 degrees to about 270 degrees relative to a radial line R extending from the center of the drum 41 to the discharge end 315 of the tube 305. For example, in the illustrated embodiment the tube 305 is oriented to extend radially relative to the forming drum 7 (e.g., co-linear with the radius R of the drum). However is contemplated that the tube 305 may be oriented with its discharge end 315 facing generally in the direction of movement of the forming surface 11, or in a direction generally counter to the direction of movement of the forming surface 11.

The delivery tube 305 of the illustrated embodiment is constructed of substantially clear polycarbonate to permit the operator to see into the central passage 309 of the tube during operation of the apparatus 301. However, the tube 305 may alternatively be constructed of other suitable materials, such as steel or other metals, plastics and the like. As seen best in FIG. 16, the delivery tube 305 is diamond-shaped in cross-section to provide a generally aerodynamic profile within the forming chamber 9 to thereby inhibit fibrous material against accumulating on the outer surface of the tube and to minimize any disruption of the air and fiber flow within the forming chamber. It is contemplated, however, that the cross-section of the delivery tube 305 may be substantially of any shape, including circular, polygonal, tear-drop, airfoil or other suitable shape. A divider in the form of a generally flat panel 335 laterally spans the central passage 309 of the delivery tube 305 and extends longitudinally from the inlet end 311 to the discharge end 315 of the tube. However, it is contemplated that the panel 335 may extend only partially along the length of the tube 305 as long as the panel terminates at or generally adjacent the discharge end of the tube.

Figure 16:
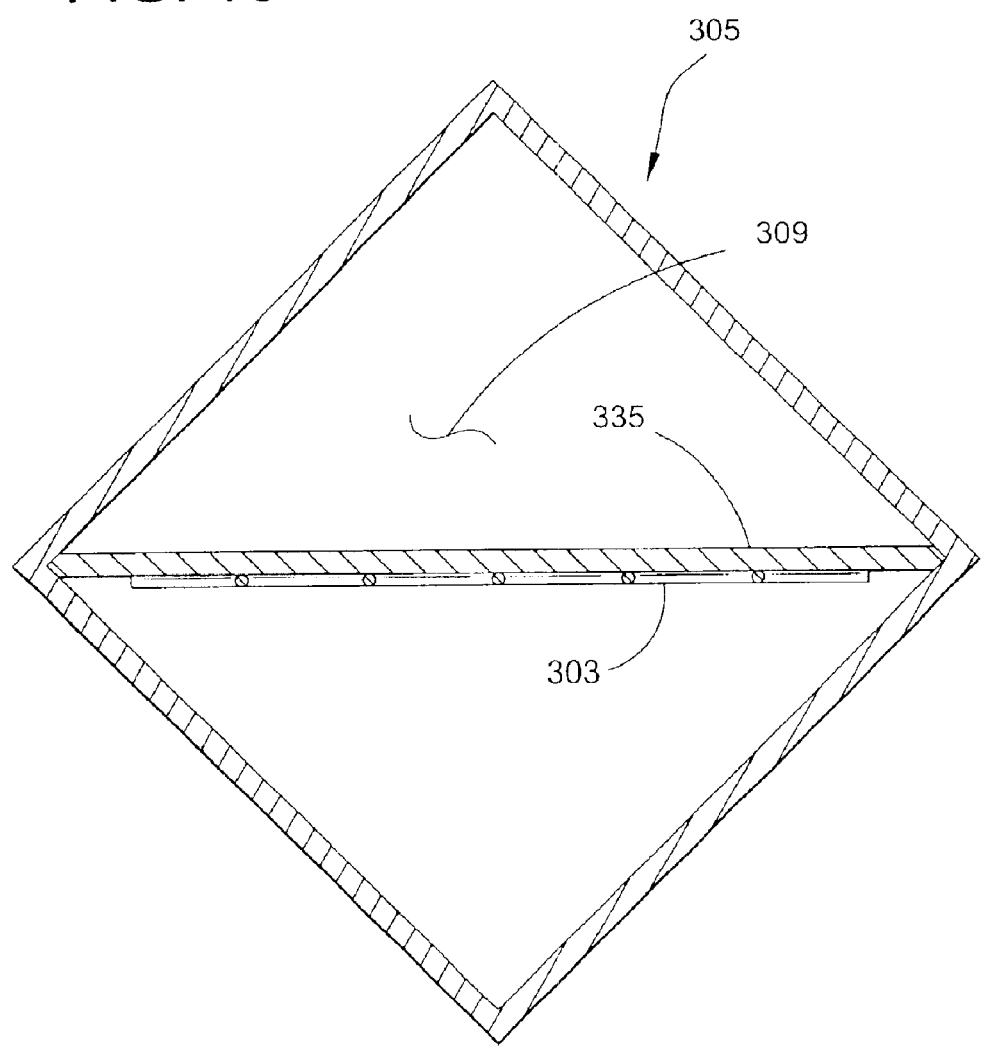
FIG. 16 is an enlarged cross sectional view of a delivery tube of the apparatus of FIG. 13.

The width of the panel 335 (and hence the cross-sectional width of the delivery tube 305) is slightly greater than the width of the reinforcing web 303 to inhibit impacting, folding or otherwise bunching of the web against the side of the tube 305. However, the panel 335 width is desirably sufficiently limited to inhibit cross-directional CD misalignment of the reinforcing web 303 relative to the article 3 as the web passes from the discharge end 315 of the delivery tube 305 toward the forming surface 11. For example, the panel 335 width (and cross-sectional width of the delivery tube 305) is desirably in the range of about 0.1 percent to about 35 percent greater than the width of the reinforcing web 303. As a further example, the width of the reinforcing web 303 shown in FIG. 16 is about 52 mm and the width of the divider panel 335 and cross-sectional width of the tube 305 is about 68 mm (e.g., about 31 percent greater than the width of the reinforcing web). As an additional example, the article into which the reinforcing web is incorporated has a width of approximately 76 mm during its formation within the forming chamber 9. The vacuum within the forming chamber 9 generally draws the reinforcing web 303 through the central passage 309 of the delivery tube 305 to the discharge end 315 thereof and then over the end of the panel 335 toward the forming surface 11 to incorporate the reinforcing web into the articles 3 being formed on the forming surface.

To initiate movement of the reinforcing web 303 within the delivery tube 305, a piece of tape (not shown) is adhered to the leading edge of the web 303 to close some of the openings adjacent the leading edge. The leading end of the web 303 is then manually unwound from the supply roll 325 and fed into the inlet end 311 of the delivery tube 305 whereby the web is more easily drawn by the vacuum through the tube into the forming chamber 9 and toward the forming surface 11. In this manner, the web is essentially self-threading in the sense that no additional mechanical apparatus is required to initially thread the web into the forming chamber 9.

The portion of the delivery tube 305 that extends within the interior of the second forming chamber 9 shields the reinforcing web 303 from the fibrous material until the web reaches the discharge end of the tube. The fibrous material instead passes around the delivery tube 305 toward the forming surface 11 so that the flow of fibrous material to the forming surface is substantially uniform or otherwise free or uninterrupted.

As the reinforcing web 303 traverses the distance from the discharge end 315 of the delivery tube 305 to the forming surface 11, the opposite (e.g., inner and outer) surfaces of the reinforcing web are exposed to the fluent fibrous material within the forming chamber. While some fibrous material permeates through the reinforcing web 303, the size of the web openings relative to the discrete fibers of the fibrous material are desirably such as to promote entanglement of additional fibers with the web. For example, the fibers may become entangled with the web 303 by inter-weaving with the web filaments or by wrapping around the filaments. The force of the vacuum is believed to provide the impetus for the entangling action of the fibers. In addition, those fibers entangled with the web 303 may also become entangled with other fibers, further promoting structural unification of the fibers and the web. The reinforcing web 303, with fibrous material entangled therein, is then laid over the forming surface 11, and more particularly it overlays the partially formed articles 3, to move conjointly with the articles along the path P of movement of the forming surface. The fibrous material entangled within the web may desirably becomes entangled with the fibrous material of the partially formed absorbent member.

Entanglement of the fibrous material with the reinforcing web 303 before the web overlays the partially formed fibrous article 3 facilitates drawing of the reinforcing web by the vacuum toward the forming surface 11 to thereby conform the reinforcing web generally to the contour of the forming surface, and more particularly to the contour of the partially formed fibrous article formed on the forming surface. However, it is understood that the web 303 may be sufficiently tensioned upon delivery into the forming chamber 9 to inhibit the web against conforming to the forming surface 11 contour whereby upon a change in depth of the forming surface, the web instead spans the depth change in a chord-like manner.

Upon further movement of the forming surface 11 within the second forming chamber 9 toward the exit 19, additional fibrous material is drawn toward the forming surface and collects on the partially formed fibrous article 3 and reinforcing web 303 to further increase the thickness of the article and to enclose or otherwise secure the reinforcing web therein. Where the reinforcing web 303 is scrim as in the illustrated embodiment or is otherwise at least semi-permeable to the fluent fibrous material, the additional fibrous material collects within and becomes entangled with the reinforcing web and/or with the fibrous material previously entangled with the web, to further secure the web within the fibrous article 3.

The span, or distance, that the reinforcing web 303 traverses in generally open space within the forming chamber 9 as the web travels from the discharge end 315 of the delivery tube 305 toward the forming surface 11 is at least partially a function of the radial spacing between the discharge end of the tube and the forming surface 11. Increasing this distance exposes the inner and outer surfaces of the reinforcing web 303 to the fluent fibrous material in the forming chamber 9 for a longer duration before the web is deposited onto the forming surface 11, or more particularly onto the fibrous article 3 formed thereon. Where the reinforcing web 303 is scrim, increasing this distance facilitates increased entanglement of the fibrous material within the scrim prior to the scrim being laid over the forming surface 11, and more particularly over the fibrous article 3 formed thereon.

However, this distance is desirably sufficiently small to inhibit fluttering, bending or otherwise cross-machine direction CD and/or Z-direction ZD misalignment of the reinforcing web 303 within the second forming chamber 9. Otherwise, the reinforcing web 303 may not properly overlay the partially formed article 3 and thus stick out the side of the article or be located at an undesirable depth within the article. As an example, the discharge end 315 of the delivery tube 305 is desirably spaced radially from the forming surface 11 a distance such that the span of reinforcing web 303 exposed to fibrous material within the forming chamber 9 as the web traverses from the discharge end of the tube onto the partially formed fibrous article 3 is in the range of about 1 cm to about 100 cm, more desirably in the range of about 1 cm to about 50 cm, still more desirably in the range of about 1 cm to about 20 cm and most desirably in the range of about 1 cm to about 10 cm.

In the illustrated embodiment, the reinforcing web 303 desirably passes through the delivery tube 305 within the lower half of the central passage 309 immediately below the divider panel 335, as shown in FIG. 16. Upon reaching the discharge end 315 of the delivery tube 305, the reinforcing web 303 is drawn over the end of the divider panel 335 toward the forming surface 11 to reduce the risk of any lateral folding or bunching of the web and to slightly tension the web to promote the web lying flat (e.g., planar) on the partially formed article 3. Where the drum 41 instead rotates counter clockwise, the reinforcing web 303 desirably passes through the tube 305 within the upper half of the central passage 309 and over the end of the panel 335 toward the forming surface 11.

For further detail regarding the construction and use of the delivery tube 305, reference may be made to pending U.S. patent application Ser. No. 10/306,269 entitled PROCESS AND APPARATUS FOR MAKING A REINFORCED FIBROUS ABSORBENT MEMBER by Michael B. Venturino et al., filed Nov. 27, 2002, the entire disclosure of which is incorporated by reference in a manner that is consistent herewith.

It will be apparent from the foregoing that there is an advantage to applying the reinforcing web at a location along the zone of separation 111, as shown in FIGS. 10 and 11. Application at this location avoids exposing the web to the air flows within the forming chambers 7, 9 which can result in fluttering or twisting of the web causing erratic and perhaps improper or imprecise placement of the web in the CD and Z directions relative to the layers L1 and L2.

FIG. 17 illustrates apparatus, generally designated 401, substantially similar to apparatus 201 described above, and corresponding parts are designated by the same reference numbers. The main difference in the apparatus 401 relates to the way in which fibrous material is fed to the inlets 101 and 105 of the first and second forming chambers 7, 9. With respect to the apparatus 201 (see FIG. 10), the forming chambers receive a supply of fibrous material from separate fiber feeding mechanisms, e.g., fiberizers 21 and 35. In the embodiment of FIG. 17, the forming chambers receive a supply of fibers from a common fiber feeding mechanism 403, such as a fiberizer, hammer mill or other suitable fiber feed device, the output of which is split to feed into two separate ducts 405, 407 connected to respective inlets 101, 105 of the forming chambers 7, 9. Other feed configurations may also be used without departing from the scope of this invention, so long as fiber is fed to the inlet of each forming chamber.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed:

1. Apparatus for air forming a reinforced fibrous article having a plurality of layers, said apparatus comprising:
    first and second substantially discrete forming chambers, each forming chamber having an entrance and exit,
    a foraminous forming surface movable through said first and second forming chambers along a forming path length,
    a first fiber inlet for introducing a fibrous material into said first forming chamber,
    a second fiber inlet for introducing a fibrous material into said second forming chamber,
    one or more vacuum sources in communication with said first and second forming chambers for drawing said fibrous material in said first forming chamber onto said forming surface to form a first layer on said forming surface and for drawing said fibrous material in said second forming chamber onto said forming surface to form a second layer on said forming surface over said first layer,
    a source of reinforcing web located generally exterior to the first and second forming chambers,
    a delivery mechanism for delivering reinforcing web from the source for application of the web toward the forming surface at a location along said forming path length.

2. Apparatus as set forth in claim 1 wherein said forming surface is on a drum rotatable to move the forming surface through said first and second forming chambers along an arcuate forming path length.

3. Apparatus as set forth in claim 2 wherein said location for application of the web is downstream of the exit of the first forming chamber.

4. Apparatus as set forth in claim 3 wherein said first and second forming chambers are separated from one another by a zone of separation along said forming path length, and wherein said location for application of the web is in said zone of separation.

5. Apparatus as set forth in claim 4 wherein said delivery mechanism comprises a rotatable guide roll mounted adjacent said forming path length for overlaying the reinforcing web on the first layer.

6. Apparatus as set forth in claim 2 wherein said delivery mechanism comprises a rotatable guide roll mounted adjacent said forming path length for overlaying the reinforcing web on fibers collected on said forming surface.

7. Apparatus as set forth in claim 2 wherein said location for application of the web is in the second forming chamber.

8. Apparatus as set forth in claim 7 wherein said delivery mechanism comprises a delivery tube having an open inlet end, a discharge end open to the interior of the second forming chamber, and a central passage extending between the inlet end and the discharge end, at least a portion of the delivery tube adjacent the discharge end thereof extending within the interior of the second forming chamber, said delivery tube being arranged for receiving the reinforcing web from the source of reinforcing web into the central passage of said tube at the inlet end thereof and guiding the web to the discharge end thereof for conveyance within the second forming chamber toward the forming surface.

9. Apparatus as set forth in claim 8 wherein the one or more vacuum sources are sufficient to draw the reinforcing web through the central passage of the delivery tube to the discharge end thereof and toward the forming surface.

10. Apparatus as set forth in claim 1 wherein said one or more vacuum sources comprises a first vacuum source associated with said first forming chamber and a second vacuum source associated with said second forming chamber.

11. Apparatus as set forth in claim 1 wherein said delivery mechanism is operable to apply the reinforcing web between the first and second layers.

12. Apparatus as set forth in claim 1 further comprising first and second fiber feed mechanisms for feeding fibrous materials into said first and second fiber inlets, respectively.

13. Apparatus as set forth in claim 1 further comprising a single fiber feed mechanism for feeding fibrous materials into said first and second fiber inlets, respectively.

14. Apparatus as set forth in claim 1 further comprising a first superabsorbent feed mechanism for introducing a superabsorbent material into said first forming chamber, and a second superabsorbent feed mechanism for introducing a superabsorbent material into said second forming chamber.

15. Apparatus as set forth in claim 14 wherein said first and second superabsorbent feed mechanisms are operable to introduce different superabsorbent materials into respective forming chambers.

16. A process of forming a reinforced fibrous article having a plurality of layers, said method comprising moving a foraminous forming surface through first and second substantially discrete forming chambers along a forming path length, each forming chamber having an entrance and exit, introducing a fibrous material into said first forming chamber, vacuum drawing said fibrous material in said first forming chamber onto said forming surface to form a first layer on said forming surface, introducing a fibrous material into said second forming chamber, vacuum drawing said fibrous material in said second forming chamber onto said forming surface to form a second layer on said forming surface superimposed on said first layer, and overlaying a reinforcing web on fibers collected on said forming surface at a location along said forming path.

17. A process as set forth in claim 16 wherein said location is downstream from the exit of the first forming chamber.

18. A process as set forth in claim 17 wherein said first and second forming chambers are separated by a zone of separation, and wherein said overlaying step comprises overlaying said reinforcing web on said fibers in said zone of separation.

19. A process as set forth in claim 18 wherein said overlaying step comprises feeding the reinforcing web to a guide roll for overlaying of the web on said first layer.

20. A process as set forth in claim 17 wherein said location is inside the second forming chamber.

21. A process as set forth in claim 20 further comprising feeding the reinforcing web to a delivery tube for guiding of the web by the tube toward said forming surface.

22. A process as set forth in claim 16 further comprising introducing a superabsorbent material into said first forming chamber, and introducing a second superabsorbent material into said second forming chamber.

* * * * *